(12) United States Patent
Kawakita et al.

(10) Patent No.: US 9,134,313 B2
(45) Date of Patent: Sep. 15, 2015

(54) METHOD OF DETECTING COLORECTAL CANCER OF STAGES 0 TO I

(75) Inventors: Masao Kawakita, Tokyo (JP); Kyoko Hiramatsu, Tokyo (JP); Keiichi Takahashi, Saitama (JP); Naotaka Hamasaki, Fukuoka (JP); Koji Yamaguchi, Fukuoka (JP); Tsunehisa Kaku, Fukuoka (JP); Koichiro Muta, Fukuoka (JP); Munechika Enjoji, Fukuoka (JP); Seiji Naito, Fukuoka (JP); Jun Hayashi, Fukuoka (JP); Shoshu Mitsuyama, Fukuoka (JP); Hiroyuki Yamashita, Oita (JP); Toru Inoue, Fukuoka (JP); Masato Kato, Fukuoka (JP)

(73) Assignees: Tokyo Metropolitan Organization For Medical Research, Tokyo (JP); CRC Inc., Fukuoka (JP); Tokyo Metropolitan Government, Tokyo (JP); Trans Genic Inc., Kumamoto (JP)

( * ) Notice: Subject to any disclaimer, the term of this patent is extended or adjusted under 35 U.S.C. 154(b) by 796 days.

(21) Appl. No.: 12/480,983

(22) Filed: Jun. 9, 2009

(65) Prior Publication Data

US 2009/0298098 A1 Dec. 3, 2009

Related U.S. Application Data

(62) Division of application No. 10/548,658, filed as application No. PCT/JP2004/003211 on Mar. 11, 2004, now abandoned.

(30) Foreign Application Priority Data

Mar. 11, 2003 (JP) .................................. 2003-065562
Oct. 28, 2003 (JP) .................................. 2003-367568

(51) Int. Cl.
*G01N 33/574* (2006.01)
*C07K 16/30* (2006.01)

(52) U.S. Cl.
CPC .............. *G01N 33/574* (2013.01); *C07K 16/30* (2013.01)

(58) Field of Classification Search
None
See application file for complete search history.

(56) References Cited

U.S. PATENT DOCUMENTS 6,355,623 B2 * 3/2002 Seidman et al. ................. 514/45
6,673,914 B1 * 1/2004 Hoon

FOREIGN PATENT DOCUMENTS

JP 11-75839 3/1999
JP H11-075839 A 3/1999

OTHER PUBLICATIONS

Jul. 18, 2007 Communication pursuant to Article 96(2) EPC issued by the European Patent Office for corresponding application No. EP 04 719 642.3.
Dec. 30, 2008 Communication pursuant to Article 94(3) EPC issued by the European Patent Office for corresponding application No. EP 04 719 642.3.
Jul. 27, 2009 Communication pursuant to Article 94(3) EPC issued by the European Patent Office for corresponding application No. EP 04 719 642.3.
Jan. 29, 2010 Communication pursuant to Article 94(3) EPC issued by the European Patent Office for corresponding application No. EP 04 719 642.3.
Kyoko Hiramatsu, et al.; "Development of aSensitive and Accurate ELISA System That Can Replace HPLC Analysis for the Determination of N1, N12-Diacetylspermine in Human Urine"; J. Biochem., vol. 124; 1998; pp. 231-236.
The International Search Report and PCT/IPEA/409 forms issued for Parent PCT Application No. PCT/JP2004/003211.
Masaru Hamaoki, et al., "Two Enzyme-Linked Immunosorbent Assay (ELISA) Systems for $N^1$, $N^8$-Diacetylspermidine and $N^1$, $N^{12}$-Diacetylspermine Using Monoclonal Antibodies," J. Biochem, 132, (2002), pp. 783-788.
Kyoko Hiramatsu, et al., "Diagnostic and prognostic usefulness of $N^1$, $N^8$-diacetylspermidine and $N^1$, $N^{12}$-Diacetylspermine in urine as novel markers of malignancy," J. Cancer Res Clin Oncol, (1997) 123, pp. 539-545.
Makasaki Kobayashi, et al., "Mass Spectrometric Separation and Determination of $N^1$, $N^{12}$-Diacetylspermine in the Urine of Cancer Patients," Biol Parm Bull, vol. 25, No. 3, (2002), 372-374.
Seon Hwa Lee, et al., "Polyamine profiles in the urine of patients with leukemia," Cancer Letters 122 (1998), pp. 1-8.
Seon Hwa Lee, et al., "Estrogens and polyamines in breast cancer: their profiles and values in disease staging," Cancer Letters 133 (1998) pp. 47-56.
Kan Shimpo, et al., "High-performance liquid chromatographic determination of diacetylpolyamines using benzoyl chloride as a derivatizing agent: application to human urine," Biogenic Amines, vol. 16, No. 3, (2001) pp. 21-223.
Kyoko Hiramatsu et al., "$N^1N^{12}$-diacetylspermine (DiAcSpm) as a tumor marker for recognizing colon cancer patients at early stages"; Seikagku, vol. 75, No. 8, p. 891, 2P-691, 2003.
Masao Kawakita et al.; "Clinical Significance of Urinary Diacetylspermine"; Japanese Journal of Clinical Chemistry, vol. 32, Supp. 2, p. 42, S4-1, 2003.
Takahashi Keiichi et al.; "Significance of Urinary Diacetylspermine as a Tumor Marker for Gastrointestinal Cancer—Colorectal Cancer Cases-"; Japanese Journal of Clincal Chemistry, vol. 32, Supp. 2, p. 44, S4-3, 2003.
Masao Kawakita et al.; "Significance of Urinary Diacetylspermine as a Tumor Marker"; Proceedings of Japanse Society of Polyamine Research—19th Research Meeting, p. 17, Feb. 6, 2004.

* cited by examiner

*Primary Examiner* — Peter J Reddig
(74) *Attorney, Agent, or Firm* — Dickstein Shapiro LLP

(57) ABSTRACT

A tumor marker comprising diacetylspermine, and a method of evaluating the state of a tumor, comprising reacting an antibody to diacetylspermine with a biological sample to thereby detect diacetylspermine and evaluating the state of the tumor using the obtained detection results as an indicator.

7 Claims, 18 Drawing Sheets

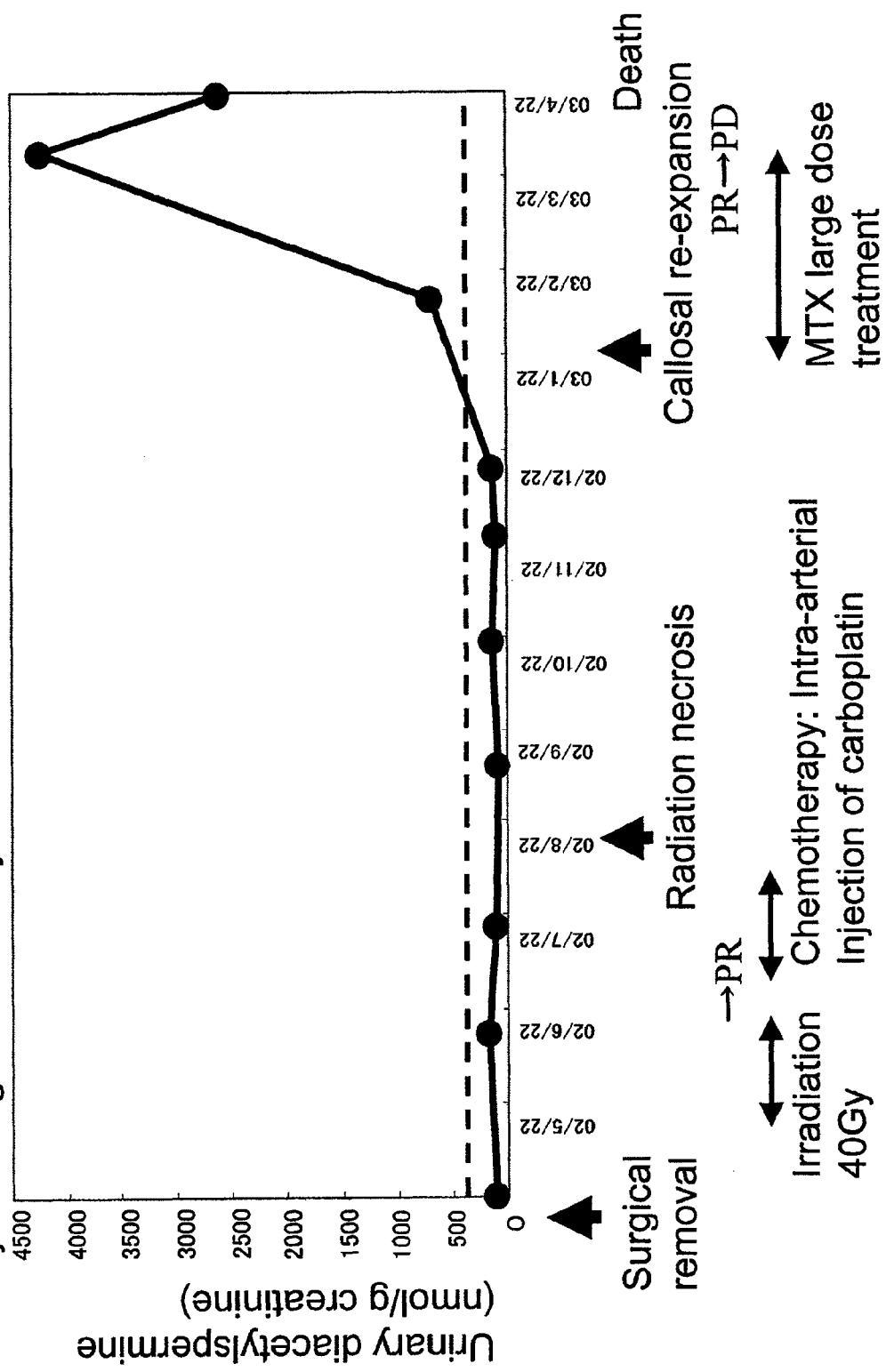

METHOD OF DETECTING COLORECTAL CANCER OF STAGES 0 TO I

CROSS REFERENCE TO RELATED APPLICATIONS

This is a Divisional Application of U.S. Ser. No. 10/548,658 filed Aug. 1, 2006 which is a National Stage Application of PCT/JP2004/003211 published as WO 2004/081569 on Sep. 23, 2004 which claims priority to Japanese Application No. 2003-065562, filing date Mar. 11, 2003, and Japanese Application No. 2003-367568, filing date Oct. 28, 2003.

TECHNICAL FIELD

The present invention relates to a tumor marker comprising $N^1,N^{12}$-diacetylspermine, a method of evaluating the state of a tumor using the tumor marker, an antibody to diacetylspermine, a method of detecting a tumor using the antibody, and a kit for detecting a tumor.

BACKGROUND ART

Polyamine is a general term for those alkylamines with two or more amino groups. There are four types of polyamines [putrescine ($H_2N(CH_2)_4NH_2$), cadaverine ($H_2N(CH_2)_5NH_2$), spermidine ($H_2N(CH_2)_4NH(CH_2)_3NH_2$) and spermine ($H_2N(CH_2)_3NH(CH_2)_4NH(CH_2)_3NH_2$)] and acetylated forms thereof in the human body.

Relatively recently, it was found that two types of diacetylpolyamines [$N^1,N^8$-diacetylspermidine (hereinafter expressed as "DiAcSpd") and $N^1,N^{12}$-diacetylspermine (hereinafter expressed as "DiAcSpm")] are excreted in urine though very small in quantities. While these components occupy only 1.4% and 0.6% of the total polyamine, respectively, in the urine of healthy persons, the ratios of these components remarkably increase in the urine of cancer patients as compared to other polyamine components. Further, it has been shown that these components have other characteristics of tumor markers (Sugimoto, M. et al., J. Cancer Res. Clin. Oncol., 121, 317-319 (1995); Hiramatsu, K. et al., J. Cancer Res. Clin. Oncol., 123, 539-545 (1997)).

Initially, DiAcSpd and DiAcSpm were quantitatively determined by a method which was a combination of a fractionation system by HPLC and a detection system using enzyme (Hiramatsu, K. et al., J. Biochem., 117, 107-112 (1995)). However, more simple measuring methods have been developed. In particular, with respect to the measurement of DiAcSpm, an ELISA method using a specific antibody was developed recently (Hiramatsu, K. et al., J. Biochem., 124, 231-236 (1998)). However, preparation of a kit containing an ELISA measuring system has not been achieved yet.

Techniques for measuring DiAcSpm by immunoassay have also been developed (Japanese Patent Unexamined Publication No. H11-75839; Japanese Patent Unexamined Publication No. 2000-74917), but they have room for improvement in terms of measurement sensitivity and cross-reactivity.

It is well known that metabolism of polyamines are activated in association with cell proliferation. In fact, polyamine contents tend to increase in various cancer tissues as compared to normal tissues. Since any of these polyamines is contained abundantly in actively proliferating tissues and is excreted in large quantity in the urine of cancer patients as compared to the urine of healthy persons, they are evaluated as tumor markers. A kit which is capable of measuring the total polyamine content easily by an enzymatic determination method without discriminating acetylated polyamines and free polyamines in urine and without discriminating the four types of polyamines in urine has already been commercialized (Labo-Search PolyamineAuto; AIT Corporation). This kit is used as one of clinical test methods. However, with respect to urinary total polyamine, it has become clear that a relatively large number of false negative results are found in malignant tumor patients and that total polyamine significantly increases in association with not only malignant tumors but also with various diseases and conditions such as inflammatory diseases, cardiac infarction, cirrhosis, process of curing of wounds, etc. Thus, it is considered that total polyamine cannot be evaluated as a marker specific to malignant tumors (Shunichiro Kubota, NIPPON-RINSHO (Japan Clinical Medicine) 53, Special Issue, pp. 501-505 (1995)). On the other hand, researchers are now revealing that some of the problems total polyamine has can be avoided by measuring diacetylpolyamines (DiAcSpd and DiAcSpm) discretely (Sugimoto, M. et al., J. Cancer Res. Clin. Oncol., 121, 317-319 (1995)).

DISCLOSURE OF THE INVENTION

The present invention aims at providing DiAcSpm as a tumor marker. The present invention also aims at providing an antibody which is extremely small in cross-reactivity with DiAcSpm analogues and yet binds specifically to a trace amount of DiAcSpm.

As a result of intensive and extensive researches toward the solution of the above-described problems, the present inventors have found that DiAcSpm is useful as a tumor marker and succeeded in creating an antibody which does not cross-react with other urinary polyamines (that are DiAcSpm analogues) and reacts only with DiAcSpm specifically. Thus, the present invention has been achieved.

The present invention relates to the following.

(1) A tumor marker comprising $N^1,N^{12}$-diacetylspermine.

(2) A method of detecting a tumor, comprising reacting an antibody to $N^1,N^{12}$-diacetylspermine with a biological sample.

In the above method, urine may be used as the biological sample. As the tumor, at least one selected from the group consisting of urinary tract malignant tumors, colorectal cancer, breast cancer, pancreatic cancer, biliary tract cancer, lung cancer, liver cancer, uterine cervix cancer, brain tumor, myelogenous leukemia and malignant lymphoma may be given. The state of a tumor is at least one selected from the group consisting of the presence/absence of cancer, the degree of progression of cancer, the degree of malignancy of cancer, the presence/absence of metastasis of cancer and the presence/absence of recurrence of cancer.

In the present invention, it is possible to evaluate early cancers (e.g., stages 0 to I in colorectal cancer and stages I to II in breast cancer).

(3) An antibody to DiAcSpm, which has at least one property selected from the following (a) and (b):
   (a) cross-reactivity with $N^1$-AcSpd: 0.1% or less
   (b) total cross-reactivity with DiAcSpm analogues present in urine: 5% or less.

As the above antibody, a polyclonal antibody or monoclonal antibody may be given.

(4) A method of detecting DiAcSpm, comprising reacting the above antibody with a biological sample (e.g., urine).

(5) A method of detecting a tumor, comprising reacting the above antibody with a biological sample (e.g., urine). As the tumor, at least one selected from the group consisting of urogenital malignant tumors, colorectal cancer, breast cancer, pancreatic cancer, biliary tract cancer, lung cancer, liver cancer, uterine cervix cancer, brain tumor, myelogenous leukemia and malignant lymphoma may be given. In the present invention, it is possible to evaluate early cancers (e.g., stages 0 to I in colorectal cancer and stages I to II in breast cancer).

(6) A tumor detection kit comprising an antibody to $N^1, N^{12}$-diacetylspermine.

As the antibody used in the kit of the present invention, an antibody having at least one property selected from the following (a) and (b) may be given:

(a) cross-reactivity with $N^1$-AcSpd: 0.1% or less
(b) total interference on the measurement results caused by its cross-reaction with DiAcSpm analogues present in urine: 5% or less.

The antibody may be a polyclonal antibody or monoclonal antibody.

As the tumor to be detected, at least one selected from the group consisting of urogenital malignant tumors, colorectal cancer, breast cancer, pancreatic cancer, biliary tract cancer, lung cancer, liver cancer, uterine cervix cancer, brain tumor, myelogenous leukemia and malignant lymphoma may be given.

Further, the kit of the present invention has at least one property selected from the following (a) to (c):

(a) lower detection limit in actual measurement: 9.06 nM
(b) within-run reproducibility: CV=10% or less
(c) between-day reproducibility: CV=10% or less.

BRIEF DESCRIPTION OF THE DRAWINGS

FIG. 18 is a diagram showing the time course of urinary DiAcSpm levels which reflect the conditions and treatment effects of an astrocytoma patient.

BEST MODES FOR CARRYING OUT THE INVENTION

Hereinbelow, the present invention will be described more specifically.

The present invention is characterized by using DiAcSpm as a tumor marker. The present invention also relates to an antibody that does not react with urinary polyamines other than DiAcSpm (DiAcSpm analogues such as $N^1$-AcSpd, $N^8$-AcSpd, $N^1,N^8$-DiAcSpd and AcSpm: see Table 1) and reacts only with DiAcSpm specifically.

The antibody of the invention has one or both of the following properties: (i) its cross-reactivity with $N^1$-AcSpd (which is present in urine as a DiAcSpm analogue in an amount about 30-times greater than DiAcSpm) is 0.1% or less; (ii) total interference on the measurement results caused by its cross-reaction with DiAcSpm analogues present in urine is 5% or less. The numerical value mentioned in (i) above is a value showing the nature of the antibody. The numerical value mentioned in (ii) above is a value obtained by multiplying cross-reactivity itself by the abundance of these analogues in urine; this value can be an indicator showing how much interference these analogues would give actually on the quantitative determination of DiAcSpm.

1. Urinary Polyamines

Figure 1:
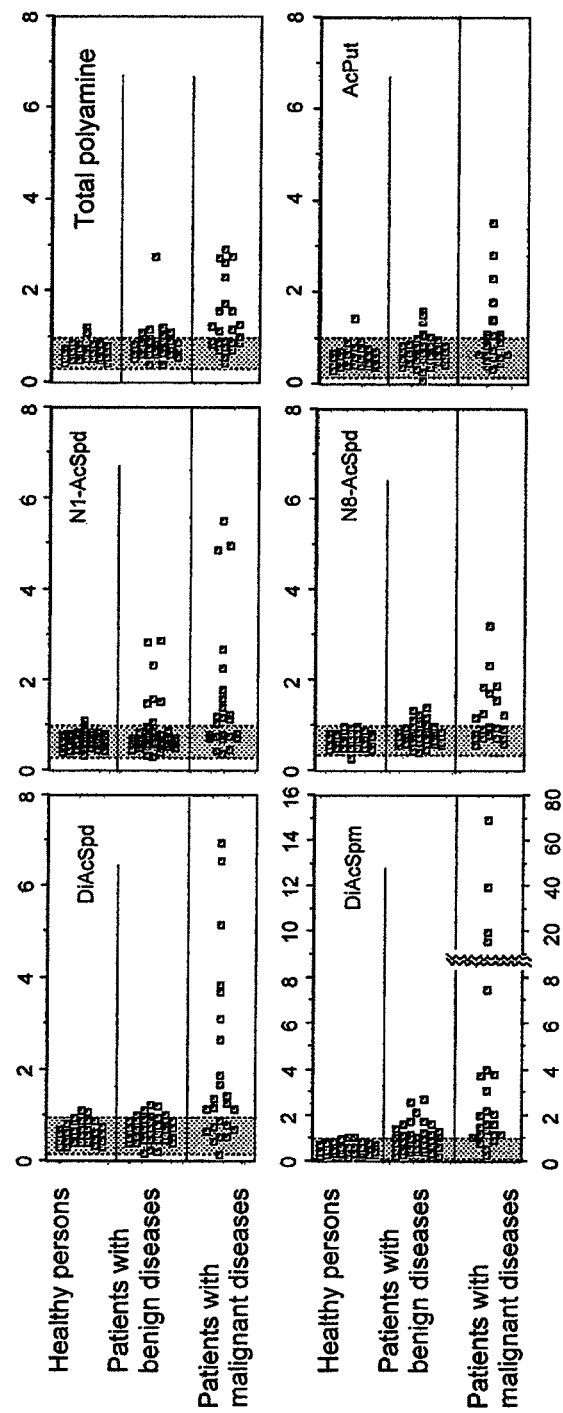
FIG. 1 shows graphs showing the amounts of polyamines excreted in urine (ratios to cut-off values).

FIG. 1 provides graphs showing the results of analysis and quantitative determination of urinary polyamine levels by HPLC: these results are summarized by component and classified into the three groups of healthy persons, patients with urogenital benign diseases, and patients with urogenital malignant tumors (e.g., prostate cancer, kidney cancer, testicular cancer). Usually, urinary polyamine levels are expressed as creatinine-corrected values which are obtained from actually measured values on random urine samples. Here, the mean of healthy persons was obtained from the thus measured levels for individual components. Taking the mean of healthy persons±2S.D. as the cut-off value, ratios of individual components to the cut-off value are plotted in graphs. For example, as to DiAcSpd and DiAcSpm, healthy person levels of 0.30±0.11 μmol/g creatinine (mean±S.D.) and 0.15±0.05 μmol/g creatinine, respectively, were obtained. Based on these levels, DiAcSpd 0.52 mol/g creatinine and DiAcSpm 0.25 mol/g creatinine are taken as cut-off values. As shown in FIG. 1, with respect to acetylputrescine (AcPut), $N^1$- and $N^8$-(mono)acetylspermidines ($N^1$-AcSpd and $N^8$-AcSpd, which are major components present most abundantly in urine) and total polyamine, a large number of false negative results occur where even cancer patients do not show high levels. Further, in many cases, tumor patients and false positive benign disease patients cannot be discriminated with those components. On the other hand, with respect to DiAcSpd and DiAcSpm, a large part of cancer patients shows high levels. In particular, DiAcSpm has remarkable characteristics; it is low in false negative ratio and very high in abnormal detection ratio. DiAcSpd is characterized by showing little increase in benign disease patients and thus being extremely low in false positive ratio (Sugimoto, M. et al., J. Cancer Res. Clin. Oncol., 121, 317-319 (1995)). Not only in urogenital malignant tumors but also in colorectal cancer and breast cancer, urinary DiAcSpm in patients elevates at a high frequency.

This means that, if it is possible to develop a method of measuring diacetylpolyamines easily and accurately, there would be a large demand for them as novel tumor makers in clinical cancer diagnosis.

Table 1 below shows the results of analysis of various polyamine components (diacetylpolyamines and their analogues) contained in the urine of healthy persons.

Table 1. Urinary Polyamine Levels in Healthy Persons

Figure 2:
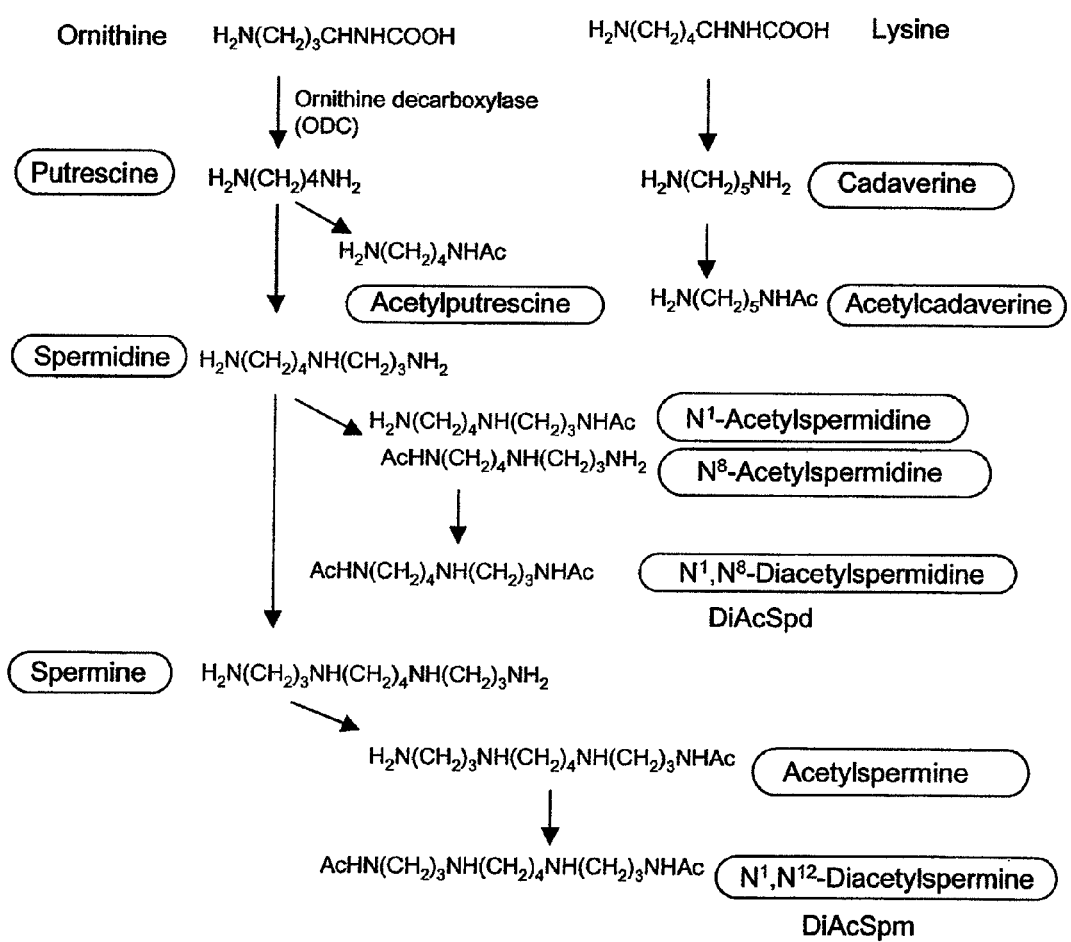
FIG. 2 is a diagram showing polyamines and their mono- and di-acetylated forms.

Major components in human urinary polyamines are various monoacetylpolyamines. DiAcSpm definitely belongs to trace components and it constitutes only 0.6% of the total polyamine. Monoacetylspermidines ($N^1$-AcSpd and $N^8$-AcSpd) which are very similar to DiAcSpm in structure are found among the major components of urinary polyamines (FIG. 2) and usually, their contents reach 25-30 times the content of DiAcSpm. Given the similarity in structure, sufficient consideration should be made on the possibility that anti-DiAcSpm antibody also cross-reacts with these monoacetylspermidines. In order to measure correctly the amount of DiAcSpm in urine where monoacetylspermidines are present as interfering substances in an amount about 30-times greater than DiAcSpm, a specific antibody is necessary which strictly discriminates the substance of interest from interfering substances with low cross-reactivity. Therefore, it is demanded to prepare an antibody which shows such specificity and yet can accurately measure DiAcSpm of concentrations around 0.1 μM (which is the urinary DiAcSpm concentration of average healthy person).

2. Tumor Marker

In order to use the DiAcSpm of the present invention as a tumor marker, it is very

|  | Mean [1] (μmol/g Creatinine) | Standard Deviation (S.D.) (μmol/g Creatinine) | Coefficient of Variation (C.V.) (%) |
|---|---|---|---|
| Total Polyamine | 22.2 | 6.1 | 27 |
| Putrescine | 0.54 | 0.52 | 97 |
| Ac-Putrescine | 9.57 | 3.52 | 37 |
| Cadaverine | 0.23 | 0.24 | 105 |
| Spermidine | 0.17 | 0.14 | 80 |
| Ac-Cadaverine | 5.55 | 2.64 | 48 |
| $N^1$-Ac-Spermidine | 2.70 | 0.84 | 31 |
| $N^8$-Ac-Spermidine | 2.41 | 0.61 | 25 |
| DiAcSpermidine | 0.301 | 0.109 | 36 |
| Spermine | 0.62 | 0.98 | 158 |
| Ac-Spermine | 0.032 | 0.077 | 237 |
| DiAcSpermine | 0.107 | 0.047 | 46 |

[1] Mean from 52 healthy persons important that the DiAcSpm contained in a sample should be detected at a high sensitivity. As a means for such detection, an antibody to DiAcSpm may be used in the present invention.

As a method for purifying DiAcSpm-specific antibody, a method is known in which rabbits are immunized with an Ac-Spermine derivative of bovine serum albumin, and then DiAcSpm-specific antibodies are purified from the resultant anti-sera (Hiramatsu, K. et al., J. Biochem., 124, 231-236 (1998)). In the present invention, a DiAcSpm-specific antibody is newly prepared based on that method, and a DiAcSpm-measuring kit comprising the antibody is prepared.

When hapten antibodies such as anti-DiAcSpm antibody are prepared, the design of the molecular structure of a hapten-carrier conjugate has a large effect upon the performance of the resultant specific antibody. It is reported that antibodies prepared using spermine bound to BSA with glutaraldehyde as a hapten show higher reactivity with spermine or spermidine than reactivity with acetylpolyamines in competitive ELISA. Therefore, in order to prepare an antibody that reacts preferentially with acetylpolyamines, it is indispensable that acylamide bond is present in the hapten-carrier conjugate.

When a polyclonal anti-serum shows about 5-6% cross-reactivity with $N^1$-AcSpd, such anti-serum cannot be used immediately for the purpose of quantitative determination of DiAcSpm. In this case, a highly specific antibody component contained in the anti-serum must be purified by some methods. As techniques to purify such a component, designing of the molecular structure of the ligand for an affinity resin is believed to be important. Briefly, it is effective to create a structure similar to acetylpolyamines by allowing to form an acylamide bond at the binding site between a polyamine ligand and a resin, as in the design of the immunizing antigen. For example, when carboxy-Toyopearl is derivatized with $N^8$-AcSpd, Spd and AcSpm, affinity resins with affinity ligands very similar to DiAcSpd, $N^1$- or $N^8$-AcSpd, and DiAcSpm in structure, respectively, will be obtained. By purifying antibodies using these affinity resins and utilizing difference in affinity for monoacetylspermidine, as well as DiAcSpd and DiAcSpm, it is possible to obtain an antibody highly specific to DiAcSpm (Hiramatsu, K. et al., J. Biochem., 124, 231-236 (1998)).

By purifying from antibodies in a crude serum an anti-DiAcSpm antibody having high specificity required for quantitative determination of urinary diacetylpolyamine, the titer of the resultant antibody naturally decreases to a considerable extent. However, in the case of the above-mentioned anti-serum, the titer of this purified antibody is considered to be sufficiently high for use in quantitative determination of DiAcSpm by standard competitive enzyme immunoassay.

In order to accurately determine DiAcSpm contained in a trace amount in urine samples where substances with similar structures represented by monoacetylspermidine are present abundantly by enzyme immunoassay, avoiding interferences by those substances, it is most important to obtain an antibody showing high specificity to DiAcSpm for establishment of a measuring kit. The present invention has established technologies for developing DiAcSpm-specific antibodies and developing kits for measuring urinary DiAcSpm, and provides a method for utilizing DiAcSpm as a tumor marker.

3. Preparation of Antigen

Since DiAcSpm is an alkylamine of a low molecular weight, immunizing rabbits with DiAcSpm does not produce DiAcSpm-specific antibodies. Therefore, an immunizing antigen which has a number of DiAcSpm-mimicking structures as side chains is prepared by binding AcSpm to bovine serum albumin (a carrier protein) via acylamide bond.

In the present invention, an immunizing antigen may be prepared based on the method of Kawakita et al. (Hiramatsu, K. et al., J. Biochem., 124, 231-236 (1998)). First, the carrier protein BSA is reacted with S-acetylmercaptosuccinic acid to thereby prepare S-acetylmercaptosuccinic acid (AMS)-BSA complex as a reaction product. Further, by coupling AcSpm to AMS-BSA by acylamide bond via a divalent crosslinking agent GMBS (N-(4-maleimidobutyryloxy) succinimide), an immunizing antigen AcSpm-GMB-BSA is prepared.

4. Preparation of Antibodies to DiAcSpm

In the present invention, the term "antibody" means any antibody molecule (either polyclonal antibody or monoclonal antibody) capable of binding to DiAcSpm (antigen) or fragment thereof (e.g., Fab or F(ab')$_2$ fragment) or active fragment thereof having antigen-antibody reaction activity (specifically, Fab, Fv, recombinant Fv, single chain Fv).

The antibody of the present invention (polyclonal antibody, monoclonal antibody and active fragment) may be prepared by any of various known methods. Methods for preparing such antibodies are well-known in the art.

Hereinbelow, the preparation of antibodies will be described more specifically with reference to experiments and Examples. However, the present invention is not limited to these experiments and Examples.

(1) Preparation of Polyclonal Antibodies to DiAcSpm

An antigen prepared as described above is administered to a mammal. The mammal is not particularly limited. Rat, mouse, rabbit, or the like may be used. Among them, rabbit is preferable.

Dose of the antigen per animal is 5-2 mg when adjuvant is not used and 5-2 mg when adjuvant is used. Examples of adjuvants useful in the invention include Freund's complete adjuvant (FCA), Freund's incomplete adjuvant (FIA) and aluminium hydroxide adjuvant. Immunization is carried out mainly by intravenous, subcutaneous or intraperitoneal injection of the antigen. The immunization interval is not particularly limited. Immunization may be carried out at intervals of several days to several weeks, preferably 2 to 5 weeks, 1 to 10 ten times, preferably 2 to 5 times. Six to sixty days after the final immunization, antibody titers are measured by such methods as ELISA (enzyme-linked immunosorbent assay), EIA (enzyme immunoassay) or RIA (radioimmuno assay). Blood is collected on the day when the maximum antibody titer is shown, and then anti-serum is obtained.

Subsequently, reactivities with proteins of the polyclonal antibodies in the resultant anti-serum are measured by methods such as ELISA, using a protein such as BSA. As described earlier, DiAcSpm is present in a trace amount in a mixture comprising DiAcSpd, Spd, Spm, etc. Therefore, in the present invention, antibodies reactive with DiAcSpm are selected with a still higher accuracy.

Briefly, antibodies which show strong reactivity with DiAcSpm and satisfy the following (i) and/or (ii) are selected: (i) cross-reactivity with $N^1$-AcSpd is 0.1% or less; (ii) total interference on the measurement results caused by cross-reaction with DiAcSpm analogues present in urine is 5% or less (preferably 3% or less).

(2) Preparation of Monoclonal Antibodies to DiAcSpm
(i) Collecting of Antibody-Producing Cells An antigen prepared as described above is administered to a mammal (e.g., rat, mouse or rabbit). Dose of the antigen per animal is 500-200 μg when adjuvant is not used and 500-200 μg when adjuvant is used. Examples of adjuvants useful in the invention include Freund's complete adjuvant (FCA), Freund's incomplete adjuvant (FIA) and aluminium hydroxide adjuvant. Immunization is carried out mainly by intravenous, subcutaneous or intraperitoneal injection of the antigen. The immunization interval is not particularly limited. Immunization may be carried out at intervals of several days to several weeks, preferably 2 to 5 weeks, 1 to 10 ten times, preferably 2 to 5 times. One to sixty days after the final immunization, preferably 1-14 days thereafter, antibody-producing cells are collected. As antibody-producing cells, splenic cells, lymph node cells, peripheral blood cells, and the like may be enumerated. Among all, splenic cells or local lymph node cells are preferable.
(ii) Cell Fusion In order to obtain hybridomas, cell fusion between antibody-producing cells and myeloma cells is performed. As the myeloma cell to be fused to the antibody-producing cell, a commonly available cell strain derived from an animal such as mouse may be used. A preferable cell strain to be used in the invention has drug selectivity, cannot survive in HAT selection medium (containing hypoxanthine, aminopterin and thymidine) in unfused conditions, and can survive there only after fusion to antibody-producing cells. Examples of myeloma cells include mouse myeloma cell strains such as P3X63-Ag.8.U1(P3U1) or NS-I.

Subsequently, the above myeloma cell and the antibody-producing cell are fused. Cell fusion is carried out by mixing $1\times10^6$ to $1\times10^7$ cells/ml of antibody-producing cells with $2\times10^5$ to $2\times10^6$ cells/ml of myeloma cells in an animal cell culture medium (such as serum-free DMEM or RPMI-1640) (preferable cell ratio of antibody-producing cells to myeloma cells is 5:1) in the presence of a cell fusion promoter. As the cell fusion promoter, polyethylene glycol with an average molecular weight of 1000-6000 daltons or the like may be used. Alternatively, it is also possible to fuse antibody-producing cells and myeloma cells in a commercial cell fusion device utilizing electric stimulation (e.g., electroporation).
(iii) Selection and Cloning of Hybridomas Hybridomas of interest are selected from the fused cells. Briefly, a cell suspension is appropriately diluted with fetal bovine serum-containing RPMI-1640 medium or the like and then plated on microtiter plates. A selection medium is added to each well. Cells are cultured with appropriate exchange of the selection medium. As a result, cells growing approx. 14 days after the start of cultivation in the selection medium may be obtained as hybridoma cells.

Subsequently, whether or not antibodies reactive with DiAcSpm are present in the culture supernatant of proliferating hybridoma cells is screened. The screening of hybridomas may be performed by conventional methods and is not particularly limited. For example, a part of the culture supernatant contained in a well in which hybridoma cells are growing may be collected and screened by enzyme immunoassay or radioimmunoassay.

The cloning of fused cells is performed by methods such as limiting dilution. Hybridomas producing such antibodies (as explained in the subsection for polyclonal antibody) that show strong reactivity with DiAcSpm and satisfy one or both of the following properties (i) and (ii) are selected and established: (i) cross-reactivity with $N^1$-AcSpd is 0.1% or less; (ii) total interference on the measurement results caused by cross-reaction with DiAcSpm analogues present in urine is 5% or less (preferably 3% or less).
(iv) Collecting of Monoclonal Antibodies As a method for collecting monoclonal antibodies from established hybridomas, a conventional cell culture method or abdominal dropsy formation method may be used.

In the cell culture method, hybridoma cells are cultured in an animal cell culture medium such as 10% fetal bovine serum-containing RPMI-1640 medium, MEM medium or serum-free medium under conventional culture conditions (e.g., 37° C., 5% $CO_2$ concentration) for 7 to 14 days. Then, antibodies are obtained from the culture supernatant.

In the abdominal dropsy formation method, approx. $1\times10^7$ hybridoma cells are administered into the abdominal cavity of an allogenic animal to the mammal from which the myeloma cell derived, to thereby expand the hybridoma cells greatly. One to two weeks thereafter, the abdominal dropsy is collected.

When purification of antibodies is necessary in the above-described method of collecting antibodies, antibodies may be purified by conventional methods such as ammonium sulfate salting out, ion exchange chromatography, gel filtration or affinity chromatography, or a combination of these methods.

5. Method of Detection of Tumors

Since DiAcSpm can be used as a clinical marker for cancer (tumor marker), it is possible to detect a tumor by reacting the antibody of the invention with a biological sample to thereby measure DiAcSpm in the biological sample and using the measurement results as an indicator. The measurement of DiAcSpm may be performed by any of the conventional hapten immunoassays and is not particularly limited. Examples of the tumor to be detected include, but are not limited to, the following.

(1) Oral Cavity, Nose and Throat

Tongue cancer, gingival cancer, malignant lymphoma, malignant black cancer (melanoma), upper jaw cancer, nasal cavity cancer, laryngeal cancer, pharyngeal cancer (2) Cranial Nerve System Glioma, meningioma (3) Thyroid Papillary adenocarcinoma of thyroid, follicular carcinoma of thyroid, medullary carcinoma of thyroid (4) Respiratory Organs Lung cancer (squamous carcinoma, adenocarcinoma, alveolar carcinoma, large cell undifferentiated carcinoma, small cell undifferentiated carcinoma, carcinoid)

(5) Breast

Breast cancer, breast Paget's disease, breast sarcoma (6) Blood

Acute myelogenous leukemia, acute promyelocytic leukemia, acute myelogenous monocytes leukemia, acute monocytes leukemia, acute lymphocytic leukemia, acute undifferentiated leukemia, chronic myelogenous leukemia, chronic lymphocytic leukemia, adult T cell leukemia, malignant lymphoma (lymphosarcoma, reticulosarcoma, Hodgkin's disease), multiple myeloma, primary macroglobulinemia (7) Digestive Organs Esophagus cancer, gastric cancer, gastrointestinal malignant lymphoma, pancreatic cancer, biliary tract cancer, gallbladder cancer, duodenum cancer, colorectal cancer, liver cancer (8) Female Genital Organs Uterus cancer, ovary cancer, uterus sarcoma (leiomyosarcoma, rhabdomyosarcoma, lymphosarcoma, reticulosarcoma)

(9) Urinary Organs

Urinary tract malignant tumor (prostate cancer, kidney cancer, bladder cancer, testis tumor, urethral cancer)

(10) Locomotorium

Rhabdomyosarcoma, fibrosarcoma, osteosarcoma, chondrosarcoma, sarcoma of synovial membrane, mucous sarcoma, liposarcoma, Ewing's sarcoma, multiple myeloma

(11) Skin

Skin cancer, skin Bowen's disease, skin Paget's disease, skin melanoma

In the present invention, the cancer to be detected and evaluated may be one selected from the above or a complication of two or more cancers. Preferably, the target cancer is at least one selected from the group consisting of colorectal cancer, urogenital malignant tumors (e.g. prostate cancer, kidney cancer, bladder cancer, testicular cancer, urethral cancer), breast cancer, pancreatic cancer, biliary tract cancer, lung cancer, liver cancer, uterine cervix cancer, brain tumor, myelogenous leukemia and malignant lymphoma.

Examples of methods for detecting tumors using the antibody of the invention will be described later, but use of the antibody is not particularly limited to those Examples.

Biological samples are taken from patients suspicious of cancer and subjects of health examination, followed by preparation of samples for DiAcSpm measurement. Examples of the biological sample useful in the invention include blood, urine and tissue. Urine is preferable because it is easy to handle and imposes less burden on patients.

Subsequently, the thus prepared sample for measurement is reacted with the above-described antibody. Measurement of DiAcSpm may be performed by conventional ELISA. First, microplates are coated with the antigen (DiAcSpm) in advance. On the other hand, DiAcSpm in the biological sample and DiAcSpm in the standard solution are pre-reacted with the anti-DiAcSpm specific antibody, and the resultant reaction solutions are plated on the microplates. The antibody remaining unreacted binds to the DiAcSpm on the microplate. Then, HRP-labeled anti-rabbit IgG antibody (which is a secondary antibody) is added to the microplate for reaction. Finally, the amount of DiAcSpm contained in the biological sample is determined by the color development reaction catalyzed by HRP.

6. Evaluation of Tumors

The state of the tumor is evaluated or diagnosed using, as an indicator, the detection results obtained by the detection method described in above subsection 5. Detection results exceeding the specific cut-off value are classified as DiAcSpm positive, and detection results below the specific cut-off value are classified as DiAcSpm negative. When the result is positive, it is judged that the relevant patient or subject may have cancer, and then the state of the tumor can be evaluated.

The state of a tumor means the presence or absence of the tumor or the progression thereof. Specifically, the presence or absence of cancer occurrence, the progression of cancer, the degree of the malignancy of cancer, the presence or absence of cancer metastasis, the presence or absence of cancer recurrence, and the like may be enumerated. In the evaluation of the above-mentioned state, one state may be selected. Alternatively, a plurality of states may be selected in an appropriate combination. In order to evaluate the presence or absence of cancer, whether the relevant patient has developed cancer or not is judged. The degree of the malignancy of cancer can be an indicator showing how much advanced the cancer is. This degree may be evaluated by staging the cancer or classifying the cancer into the so-called early cancer or advanced cancer. Cancer metastasis is evaluated by whether neoplasms are occurring at distant sites from the primary lesion. Recurrence is judged by whether or not the cancer appeared again after intermission or remission.

In the present invention, in the case of colorectal cancer for example, the cancer can be detected and evaluated even at stage 0 or I (early cancer) in the same manner as the cancer at stage II to IV (advanced cancer). In the case of breast cancer, the cancer can be detected and evaluated even at stage I or II (early cancer) in the same manner as the cancer at stage III to IV (advanced cancer).

7. Reagent and Kit for Tumor Detection Comprising the Antibody of the Invention

In the present invention, it is possible to use an antibody to DiAcSpm as a reagent for tumor detection.

Conventionally, when polyamines are measured in general biochemical tests, urinary polyamines were measured collectively as a single class of components. Relations between each of those similar structures and disease conditions have hardly been examined. Then, a method has been established in which amounts of urinary polyamines are measured discretely. It has been confirmed that, in particular, DiAcSpm (one species of polyamine) is highly elevated at the time of occurrence and at the time of recurrence after treatment of prostate cancer or colorectal cancer. This means that, if it is possible to develop a method of measuring diacetylpolyamines easily and accurately, there would be a large demand for them as novel tumor makers in clinical cancer diagnosis.

In conventional measuring methods, immunological techniques which enable the handling of a great number of samples with cheap measuring instruments are employed. A simple measuring method using a polyclonal antibody has already been known (Hiramatsu, K. et al., J. Biochem., 124, 231-236 (1998)). However, an ELISA measuring system has not been put into a kit; also, mass production of DiAcSpm (a most important component in the measuring system) has not been achieved.

In the present invention, the inventors contemplated a system for measuring urinary DiAcSpm by competitive ELISA using DiAcSpm antibody, based on Kawakita et al.'s simple immunological measuring method as a model. As a solid phase antigen, monoacetylspermine coupled to a peptide by acylamide bond and having a DiAcSpm-mimicking structure (AcSpm-HMC-peptide) may be used. This antigen is obtained by coupling monoacetylspermine to a water-soluble peptide by acylamide bond via bivalent crosslinking reagent (HMCS) (Hiramatsu, K. et al., J. Biochem., 124, 231-236 (1998)).

The DiAcSpm measuring kit of the invention must be capable of measuring DiAcSpm with high sensitivity. Further, this kit is required to have reproducibility if it is intended to be used in clinical scenes of cancer diagnosis. Upon such a premise, the present invention aimed at establishment of a measuring system for DiAcSpm as a diagnosis marker.

The DiAcSpm measurement ELISA kit of the invention is capable of setting its standard region ranging from 4.53 to 145 nM by adjusting the solid phase antigen concentration toward the low concentration side. The solid phase antigen concentration is 1-0.1 µg/ml, preferably 0.07 µg/ml. As a result, sensitivity and measuring accuracy sufficient to measure urinary DiAcSpm can be achieved.

Measurement accuracy is an indicator which shows to what extent individual measured values would vary when one assay has been performed using one same sample aliquoted into a plurality of test tubes or wells. Statistically, measurement accuracy is expressed as coefficient of variation (CV), that is, ratio (%) of standard deviation to mean. In the present invention, this CV is referred to as reproducibility. Reproducibility is preferably 10% or below, more preferably 5% or below.

The kit of the present invention has the following performances: lower detection limit in actual measurement: 9.06 nM that corresponds to a lower detection limit in urine or other sample of 36.2 nM (9.06 nM×4). Within-run reproducibility is 10% or less, preferably around 5%. Between-day reproducibility is 10% or less, preferably about 8-10%. In both reproducibilities, CV is 10% or less. With respect to the influence of co-existing substances, conjugated bilirubin, glucose, hemoglobin and ascorbic acid do not give any influence upon DiAcSpm measurement.

The kit of the invention may also contain antigen-coated microplates, DiAcSpm standard product (STD), antibody dilutions, HRP-labeled anti-rabbit IgG antibody, OPD (ortho-phenylene-diamine) tablets, substrate solution, reaction termination solution, concentrated washing solution or the like selected appropriately, in addition to the antibody of the invention.

Hereinbelow, the present invention will be described more specifically with reference to the following Examples. However, the present invention is not limited to these Examples.

Example 1

Preparation of Antibodies (1) Preparation of Immunizing Antigen and Immunization In this Example, the inventors examine more efficient preparation of anti-DiAcSpm antibodies in order to put into practical use the technique of extracting specific components from polyclonal antibodies by affinity purification to practical use in the production of anti-DiAcSpm polyclonal antibodies. For putting into practice use the technique of extracting specific components from polyclonal antibodies by affinity purification, extremely important things are (i) to make it clear if anti-DiAcSpm antibodies showing high specificity can be obtained reproducibly and (ii) to ascertain at what frequency mammals producing such antibodies can be obtained when mammals are immunized with one same antigen. Then, the present inventors have paid attention to the following three points in examining the efficiency and reproducibility of antibody production toward industrial production of measuring kits.

(a) The probability that antibody titers rise is low because the antigen of interest is a low molecular weight molecule.
(b) Antibody titer rising ratios vary depending on the species of rabbit to be immunized.
(c) Antibody titer rising ratios vary depending on the lot of the immunizing antigen.

In order to examine the condition (a) described above, eight rabbits of Japanese White Rabbit species (male: standard 2.5-3.0 kg, hereinafter abbreviated to "JPW") were immunized with immunizing antigen Lot 1 under same conditions. Then, whether antibody titer rising ratios vary among individual rabbits or not was examined.

In order to examine the condition (b) described above, nine rabbits of New Zealand White Rabbit species (male: standard 2.5-3.0 kg, hereinafter abbreviated to "NZW") and ten rabbits of Japanese White Rabbit species (male: standard 2.5-3.0 kg, hereinafter abbreviated to "JPW") were chosen as animal species to be immunized. Then, whether antibody titer rising ratios vary between animal species was examined.

In order to examine the condition (c) described above, five different lots of immunizing antigen AcSpm-GMB-BSA were newly prepared. Then, whether antibody titer rising ratios vary among individual animals immunized with different lots was examined.

The immunizing antigen was prepared as described below, based on the method of Kawakita et al. (Hiramatsu, K. et al., J. Biochem., 124, 231-236 (1998)). Since DiAcSpm is an alkylamine of a low molecular weight, it is impossible to obtain DiAcSpm-specific antibodies by immunizing rabbits with DiAcSpm itself. Therefore, an immunizing antigen, AcSpm-GMB-BSA, which has a number of DiAcSpm-mimicking structures as side chains was prepared by coupling AcSpm to bovine serum albumin (hereinafter abbreviated to "BSA") (a carrier protein) via acylamide bond. Briefly, BSA which functions as a carrier protein was reacted with S-acetylmercaptosuccinic acid to therein obtain the reaction product S-acetylmercaptosuccinylated BSA (hereinafter abbreviated to AMS-BSA). Further, AcSpm was coupled to AMS-BSA by acylamide bond via a bivalent crosslinking reagent GMBS to thereby obtain the immunizing antigen AcSpm-GMB-BSA.

Immunization was carried out by injecting subcutaneously in the back of animals an emulsion prepared by mixing equal volumes of the immunizing antigen and adjuvant (for first immunization: complete adjuvant; for booster immunization: incomplete adjuvant). Immunizations were carried out at the intervals of two weeks at doses of 1 mg/animal for the first immunization and 0.3 mg/animal for booster immunizations.

Seven days after the third immunization, partial exsanguination was carried out, followed by checking of the antibody titers in antisera by ELISA (Table 2).

Antibody titers are shown using the antiserum obtained by Kawakita et al. as a standard. Specifically, the reactivity of each rabbit antiserum is expressed as a percentage taking the reactivity of the Kawakita et al.'s antiserum at a dilution of 27.000-fold as 100.

As a result, the rise of antibody titer was low in JPW1-JPW8 and NZW1 immunized with antigen Lot No. 1; the highest antibody titer shown in these rabbits was 12.5% in JPW7. On the other hand, high antibody titers of 69.1% (JPW9) and 88.1% (NZW2) could be obtained in both species immunized with antigen Lot No. 2.

The results of this experiment revealed that there is difference in the rise of antibody titers depending on the lot of the antigen. However, the checking of antibody titers using the partially exsanguinated samples revealed no remarkable difference in the rise of antibody titers among rabbit individuals or between species.

TABLE 2

Immunizing Antigen and Antibody Titer in Antiserum

| Code No. | Immunizing Antigen Lot | Antibody Titer (%) in Antiserum |
|---|---|---|
| JPW1 | No. 1 | 4.71 |
| JPW2 | No. 1 | 3.73 |
| JPW3 | No. 1 | 6.52 |
| JPW4 | No. 1 | 6.98 |
| JPW5 | No. 1 | 3.20 |
| JPW6 | No. 1 | 4.29 |
| JPW7 | No. 1 | 12.5 |
| JPW8 | No. 1 | 9.09 |
| JPW9 | No. 2 | 69.1 |
| JPW10 | No. 3 | 6.86 |
| NZW1 | No. 1 | 7.59 |
| NZW2 | No. 2 | 88.1 |
| NZW3 | No. 3 | 5.76 |
| NZW4 | No. 4 | 28.4 |
| NZW5 | No. 5 | 7.11 |
| NZW6 | No. 6 | 7.41 |
| NZW7 | No. 6 | 9.70 |
| NZW8 | No. 7 | 27.8 |
| NZW9 | No. 7 | 34.0 |

(2) Purification of Anti-DiAcSpm Polyclonal Antibodies

Figure 3:
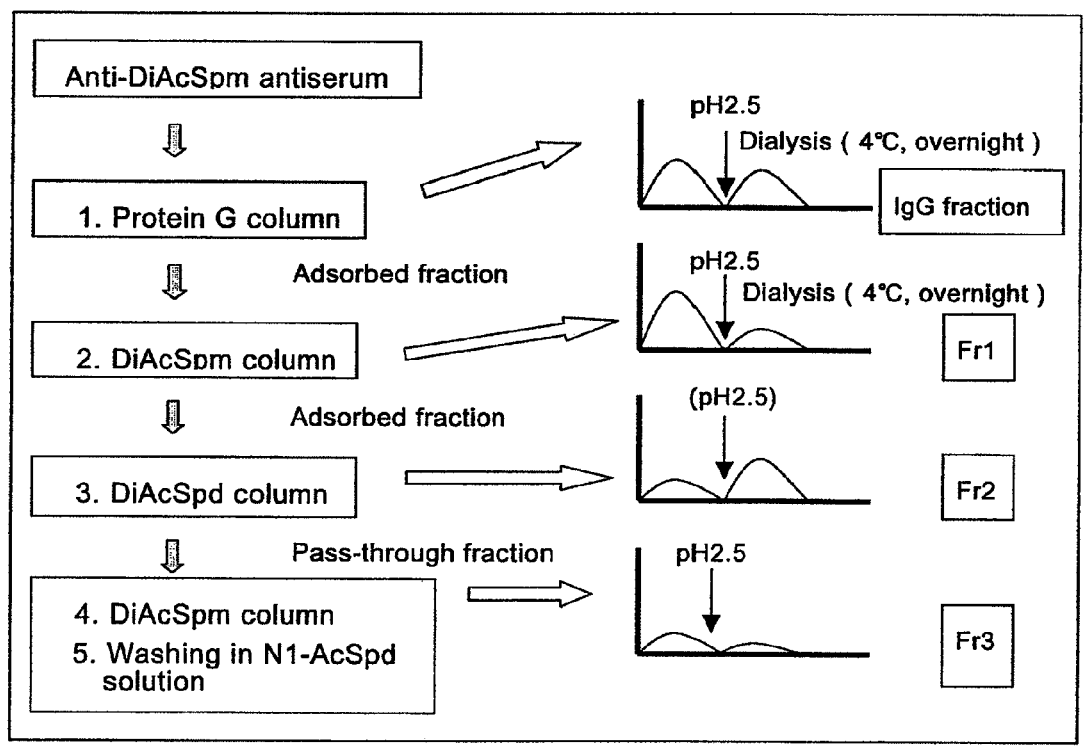
FIG. 3 is a diagram showing steps of gradual affinity purification.

Among the antisera obtained from 19 rabbits, three anti-DiAcSpm polyclonal antisera (JPW9, NZW2 and NZW9) showed high antibody titers. Step-wise affinity purification was carried out to examine whether specific antibodies with sufficient purity applicable to a urinary DiAcSpm measuring system can be obtained. The affinity purification was carried out step-wise based on the method of Kawakita et al. (Hiramatsu, K. et al., J. Biochem., 124, 231-236 (1998)), using DiAcSpm column and DiSpd column prepared by derivatizing carboxy-Toyopearl with AcSpm and N8-AcSpd (FIG. 3).

Figure 4:
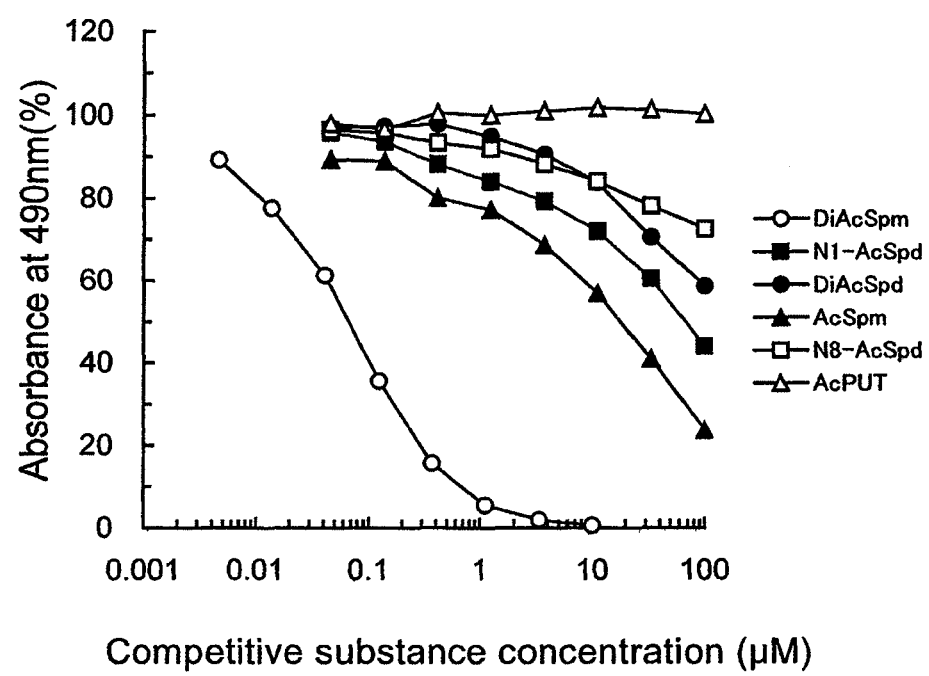
FIG. 4 is a diagram showing the cross-reactivity of anti-DiAcSpm antibody.

The results revealed that antiserum NZW2 contained an antibody whose cross-reactivity with $N^1$-AcSpd (which is present in urine as a DiAcSpm analogue in an amount about 30-times greater than DiAcSpm) is 0.1% or less. Further, the total interference on the measurement results caused by the cross-reaction of this antibody with DiAcSpm analogues present in urine was 2.9%; thus, cross-reactivity of 5% or less was achieved (FIG. 4, Table 3).

TABLE 3

Cross-Reactivity of Anti-DiAcSpm Code No. NZW 2

|  | DiAcSpm | AcSpm | N1-AcSpd | DiAcSpd | N8-AcSpd | AcPut |
|---|---|---|---|---|---|---|
| $Ki_{DiAcSpm}/Ki_{"s"}$(%) (1) | 100 | 0.418 | 0.100 | 0.032 | 0.001 | — |
| Ratio of DiAcSpm in urine (2) | 1.00 | 0.314 | 26.5 | 2.95 | 23.7 | 93.8 |
| Cross-reactivity (1)(~2)% | 100 | 0.131 | 2.65 | 0.094 | 0.024 | — |
|  |  |  |  |  | Total | 2.90% |

Thus, it was possible to prepare an anti-DiAcSpm specific antibody with high specificity applicable to the measurement of urinary DiAcSpm by immunizing rabbits with a newly prepared immunizing antigen AcSpm-GMB-BSA. This proved the efficacy of the immunizing antigen having DiAcSpm-mimicking structures as side chains, which Kawakita et al. have invented in order to obtain anti-DiAcSpm specific antibodies.

Example 2

Measurement of DiAcSpm Using the Kit

1. Establishment of Measuring Parts and Basic Data of ELISA Measuring System

As a measuring method, competitive ELISA using a solid phase antigen AcSpm-HMC-peptide was performed based on the method of Kawakita et al. (Hiramatsu, K. et al., J. Biochem., 124, 231-236 (1998)). As the primary antibody, the anti-DiAcSpm specific antibody prepared in Example 1 was used. As the secondary antibody, a commercial, goat-derived HRP-labeled anti-rabbit IgG antibody (Bio-Rad) was used. The concentration of the solid phase antigen was selected as follows. Since the normal urinary DiAcSpm level is approx. 100 nM, a range of authentic DiAcSpm concentrations from 6.25 nM to 200 nM was chosen. Then, a concentration of the solid phase antigen (0.07 μg/ml) which yields the most idealistic competitive curve with DiAcSpm in this concentration range was selected. With respect to the concentration of the anti-DiAcSpm antibody, 0.02 μg/ml was selected so that 50% of the maximum reaction efficiency is achieved when the concentration of the solid phase antigen is 0.07 μg/ml.

With respect to the HRP-labeled anti-rabbit IgG (secondary antibody), its sensitivity was examined in a range from 2000-fold to 5000-fold dilution. As a result, the highest sensitivity was obtained at 2000-fold dilution. Therefore, HRP-labeled anti-rabbit IgG 2000-fold dilution was selected as the condition of the secondary antibody.

Further, in order to evaluate the accuracy and performance of the DiAcSpm measurement ELISA, within-day reproducibility and between-day reproducibility were obtained using two different control samples (called Sample A and Sample B) and evaluated (N=20). Further, in addition-recovery tests, DiAcSpm standard product of a known concentration was added to the urine of healthy persons, followed by determination of the recovery ratio. In order to evaluate the performance of the kit, dilution tests were also performed on three urine samples with different DiAcSpm concentrations.

In order to compare HPLC (which has already been established as a method for determining urinary DiAcSpm) with the kit of the present invention, correlation was examined on 30 samples. Further, the influence of conjugated bilirubin, glucose, hemoglobin and ascorbic acid (which are co-existing substances in urine) upon the measurement system was confirmed.

2. Results

Figure 5:
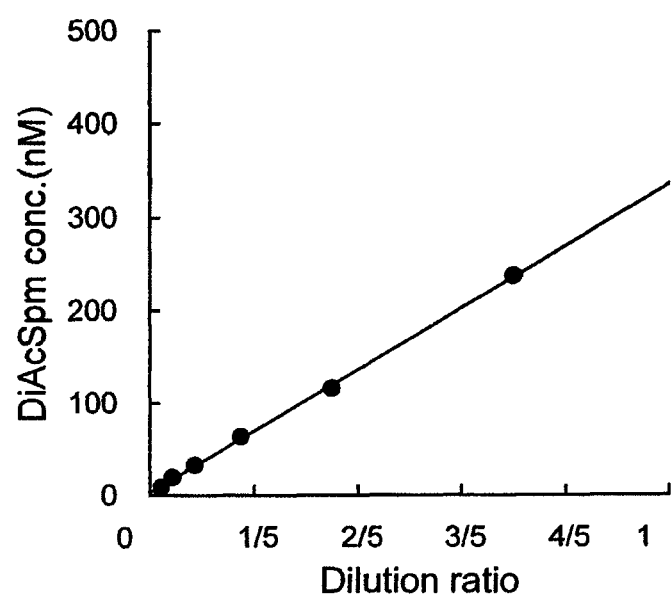
FIG. 5 is a diagram showing the results of dilution test.
Figure 6:
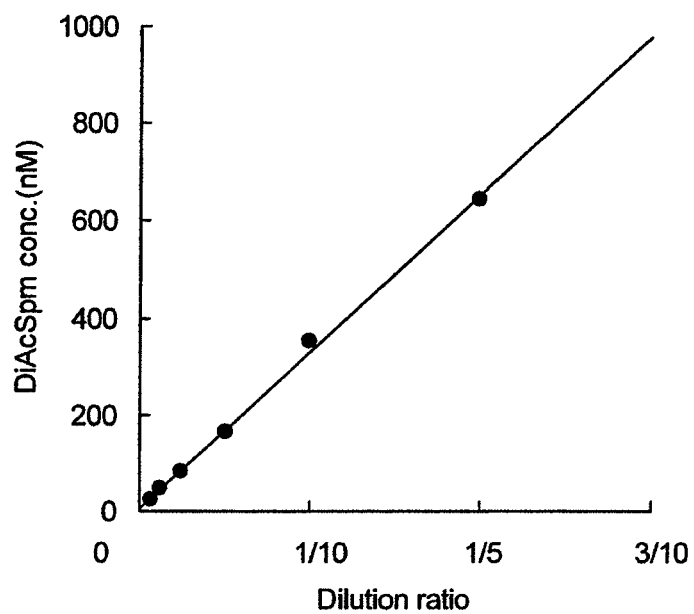
FIG. 6 is a diagram showing the results of dilution test.
Figure 7:
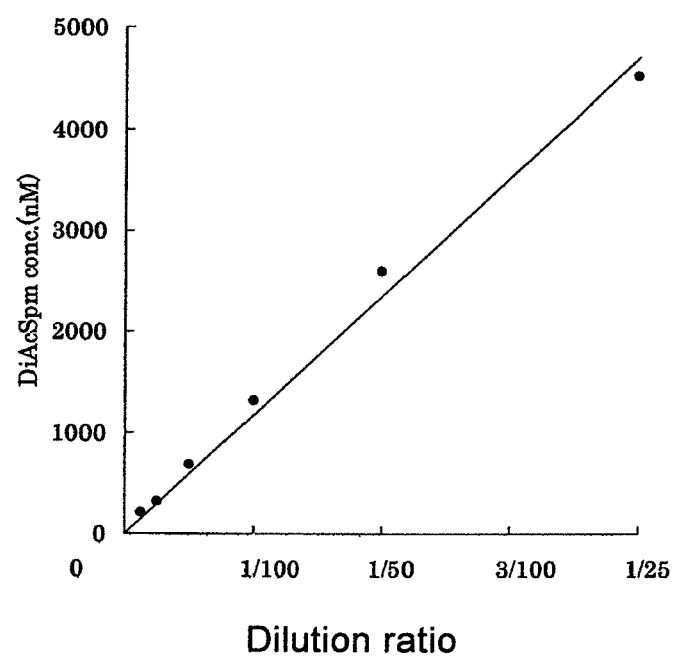
FIG. 7 is a diagram showing the results of dilution test.
Figure 8:
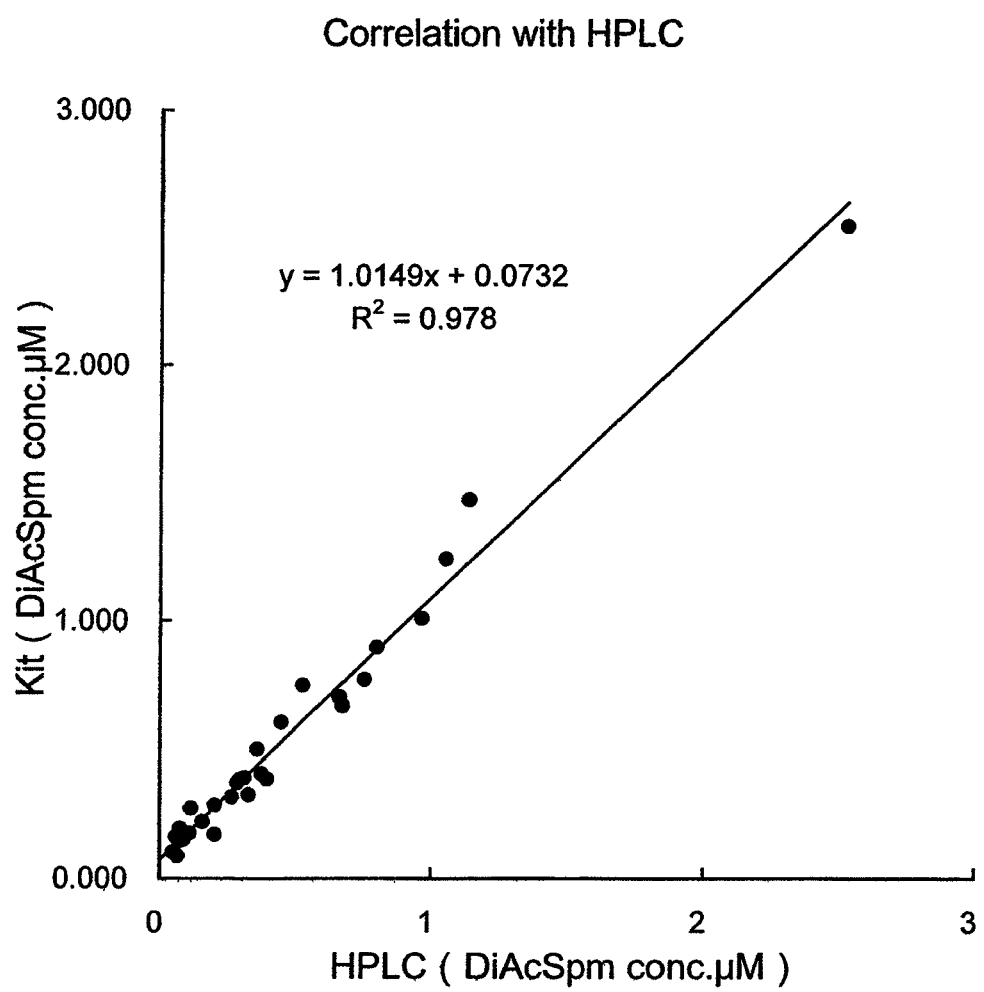
FIG. 8 is a diagram showing correlation with the values obtained by HPLC.

With respect to the performances of the assay system according to the kit of the invention, the standard curve showed linearity in the range from 6.25 to 200 nM, and both within-day and between-day reproducibilities were good (CV-10% or less). In the dilution test using three urine samples with different DiAcSpm concentrations, a good dilution curve was obtained for every urine sample as a result of measurement of serially diluted samples on each of the three (FIGS. 5 to 7).

In the addition-recovery test, 4-fold or more dilution of urine yielded good results of addition-recovery ratios 96.3-108% without individual difference. Therefore, it was decided to begin the dilution of urea at 4-fold or more.

The performances of the kit of the invention were as follows: actually measured minimum detection value: 12.5 nM; detection sensitivity in sample measurement: 50 nM (12.5 nM×4). The within-run reproducibility was CV=4.87% on Sample A and CV=5.20% on Sample B. The between-day reproducibility was CV=7.53% on Sample A and CV=9.46% on Sample B.

Therefore, it was confirmed that both reproducibilities satisfied the target value of 10% or less on each of the Samples (Table 4). With respect to co-existing substances, it was confirmed that conjugated bilirubin (10 mg/dL or less), glucose (1000 mg/dL or less), hemoglobin (400 mg/dL or less) and ascorbic acid (100 mg/dL or less) give no influence upon DiAcSpm measurement at the indicated concentrations.

Further, in order to evaluate the ELISA kit for measuring DiAcSpm, urine samples measured by HPLC which serve as reference were measured by the ELISA kit, and then the results obtained from both methods were compared and examined. As a result, correlation with HPLC was Y(nM) □1.01X+73.2, $R^2$=0.978. This is a very good result. From these results, it was demonstrated that the DiAcSpm measurement kit of the invention is capable of measuring urinary DiAcSpm with high accuracy.

The details of basic data obtained in these experiments are shown in Table 4 and FIGS. 5 to 8.

TABLE 4

| Within-day reproducibility (N = 20) | | | Between-day reproducibility (N = 20) | | |
|---|---|---|---|---|---|
| Sample | DiAcSpm conc. (nM) | | Sample | DiAcSpm conc. (nM) | |
| No. | A | B | No. | A | B |
| 1 | 94.0 | 34.5 | 1 | 102 | 37.7 |
| 2 | 89.0 | 33.0 | 2 | 104 | 29.9 |
| 3 | 95.3 | 35.2 | 3 | 100 | 31.0 |
| 4 | 97.9 | 34.3 | 4 | 110 | 33.1 |
| 5 | 103 | 32.4 | 5 | 90.6 | 29.0 |
| 6 | 96.6 | 32.1 | 6 | 94.7 | 31.3 |
| 7 | 89.8 | 31.4 | 7 | 95.5 | 32.2 |
| 8 | 91.6 | 32.5 | 8 | 92.7 | 29.5 |
| 9 | 89.8 | 30.8 | 9 | 110 | 39.3 |
| 10 | 104 | 30.9 | 10 | 108 | 37.7 |
| 11 | 96.9 | 31.5 | 11 | 94.5 | 35.6 |
| 12 | 99.5 | 34.4 | 12 | 104 | 32.6 |
| 13 | 94.6 | 30.8 | 13 | 106 | 39.3 |
| 14 | 103 | 32.1 | 14 | 115 | 32.5 |
| 15 | 93.1 | 29.9 | 15 | 93.1 | 32.1 |
| 16 | 91.9 | 31.5 | 16 | 89.2 | 31.6 |
| 17 | 95.0 | 29.7 | 17 | 100 | 36.2 |
| 18 | 92.8 | 33.3 | 18 | 113 | 36.9 |
| 19 | 100 | 32.0 | 19 | 99.3 | 33.7 |
| 20 | 91.3 | 35.3 | 20 | 96.8 | 34.0 |
| mean | 95.5 | 32.4 | mean | 101 | 33.8 |
| SD | 4.65 | 1.68 | SD | 7.6 | 3.19 |
| CV (%) | 4.87 | 5.20 | CV (%) | 7.53 | 9.46 |

Example 3

Detection of Colorectal Cancer

Relations between stages of colorectal cancer (according to "Japanese Classification of Colorectal Carcinoma" by Japanese Society for Cancer of the Colon and Rectum) and urinary DiAcSpm levels (creatinine-corrected values of concentrations in random urine) were examined on 250 patients with colorectal cancer. The cut-off value of DiAcSpm was set at 0.25 μmol/g creatinine (mean of healthy persons+2SD), and levels exceeding this were regarded as positive and levels below this were regarded as negative. As a result, out of 250 cases examined, DiAcSpm positive cases were 185 (74.0%); CEA positive cases were 94 (37.6%); and CA-19-9 positive cases were 36 (14.4%) (Tables 5 to 7). Thus, compared with existing tumor markers, DiAcSpm exhibited remarkably high detection sensitivity. Further, examination of relations between stages of patients and positive ratios based on findings obtained by pathological tests revealed that urinary DiAcSpm shows high positive ratios in both early and advanced cancers, as shown in Table 5. This demonstrates that DiAcSpm levels in the urine of colorectal cancer patients rise at high frequency even at the stages of early cancer.

TABLE 5

Positive Ratio of Urinary DiAcSpm by Stage of Colrectal Cancer

| | Positive | Negative | Positive Ratio (%) | |
|---|---|---|---|---|
| stage 0 | 13 | 8 | 62 | Early staged cancer |
| stage I | 24 | 16 | 60 | |
| stage II | 42 | 18 | 70 | Advanced cancer |
| stage III | 92 | 21 | 81 | |
| stage IV | 14 | 2 | 88 | |
| Total | 185 | 65 | | |

In Table 5, "Stage 0" means the depth of invasion is m. In other words, lesions are limited to the mucosal layer of the intestinal tract. "Stage I" means that the degree of invasion is up to the submucosal layer (sm) or the proper muscle layer (mp) and that the cancer is no tumor (with no lymph node metastasis). "Stage 0" and "Stage I" are classified into early staged cancer. If cancer is found at these stages, it is established clinically that good prognosis is expected in every case.

Further, for the purpose of comparison, relations between serum CEA or serum CA19-9 levels (now used clinically) and stages of colorectal cancer were examined on the same group of patients as examined above. With respect to CEA, the standard value was set at 5 ng/ml and levels exceeding this were regarded as positive and levels below this were regarded as negative. With respect to serum CA19-9, the standard value was set at 37 U/ml and levels exceeding this were regarded as positive and levels below this were regarded as negative.

As a result, as shown in Tables 6 and 7, positive ratios were low in early cancer in both serum CEA and serum CA19-9.

TABLE 6

Positive Ratio of Serum CEA by Stage of Colorectal Cancer

| | Positive | Negative | Positive Ratio (%) | |
|---|---|---|---|---|
| Stage 0 | 2 | 19 | 9.5 | Early staged cancer |
| Stage I | 4 | 36 | 10 | |
| Stage II | 25 | 35 | 42 | Advanced cancer |
| Stage III | 53 | 60 | 47 | |
| Stage IV | 10 | 6 | 63 | |
| Total | 94 | 156 | | |

TABLE 7

Positive Ratio of Serum CA19-9 by Stage of Large Bowel Cancer

| | Positive | Negative | Positive Ratio (%) | |
|---|---|---|---|---|
| stage 0 | 1 | 20 | 4.8 | Early staged cancer |
| stage I | 3 | 37 | 7.5 | |
| stage II | 3 | 57 | 5.0 | Advanced cancer |
| stage III | 24 | 89 | 21 | |
| stage IV | 5 | 11 | 30 | |
| Total | 36 | 214 | | |

While the positive ratio of urinary DiAcSpm for early staged colorectal cancer was about 60%, the positive ratios of serum CEA and serum CA19-9 were about 10% and about 5-8%, respectively. This demonstrates that DiAcSpm is by far superior in clinical diagnosis of colorectal cancer to the currently used tumor markers CEA and CA19-19, compared to their positive ratios for early staged large bowel cancer. Therefore, by using urinary diacetylspermine as a tumor marker and detecting the diacetylspermine with the antibody of the invention, it becomes possible to detect colorectal cancer with still higher sensitivity and at early stages. Start of treatment at early stages will increase the ratio of completely cured cases. Thus, use of this marker can greatly contribute to the clinical diagnosis of colorectal cancer.

Further, by adding urinary diacetylspermine as one of health examination items, it is possible to make early diagnosis of digestive organ cancers including colorectal cancer more sensitive and accurate by far than the diagnosis currently done.

Example 4

Detection of Breast Cancer

Figure 9:
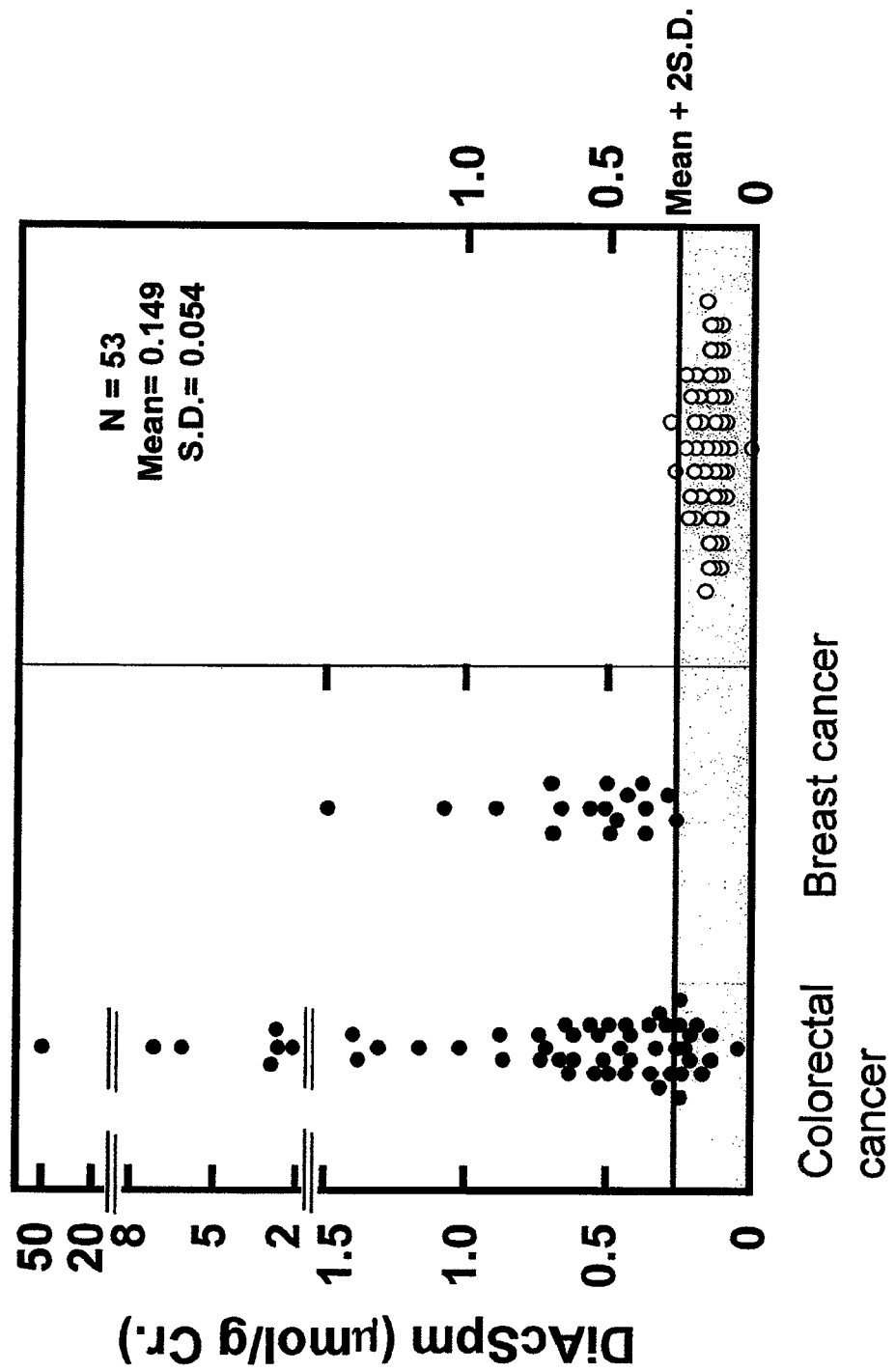
FIG. 9 is a diagram showing the results of detection of colorectal cancer and breast cancer.
Figure 10:
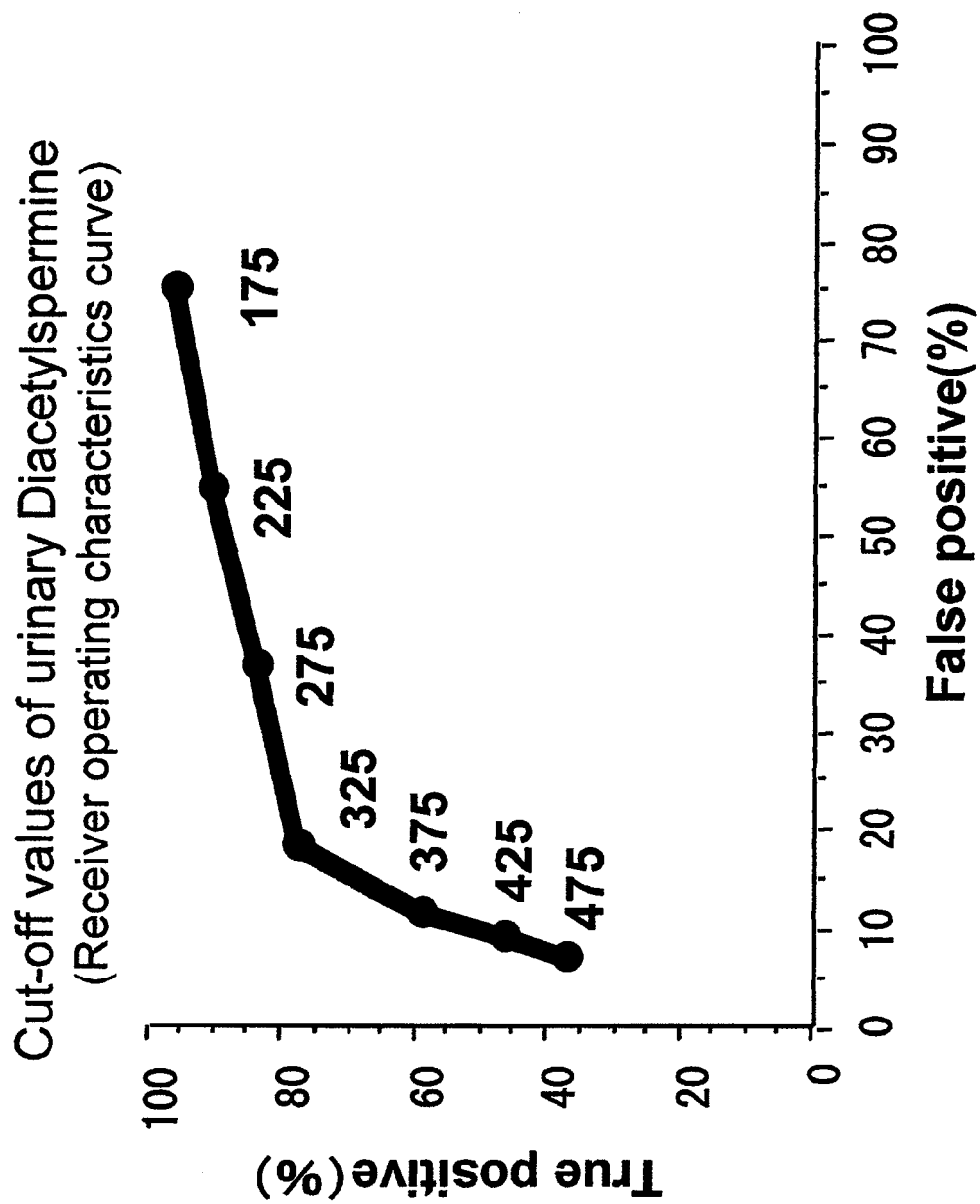
FIG. 10 is a diagram showing the cut-off values of urinary DiAcSpm.
Figure 11:
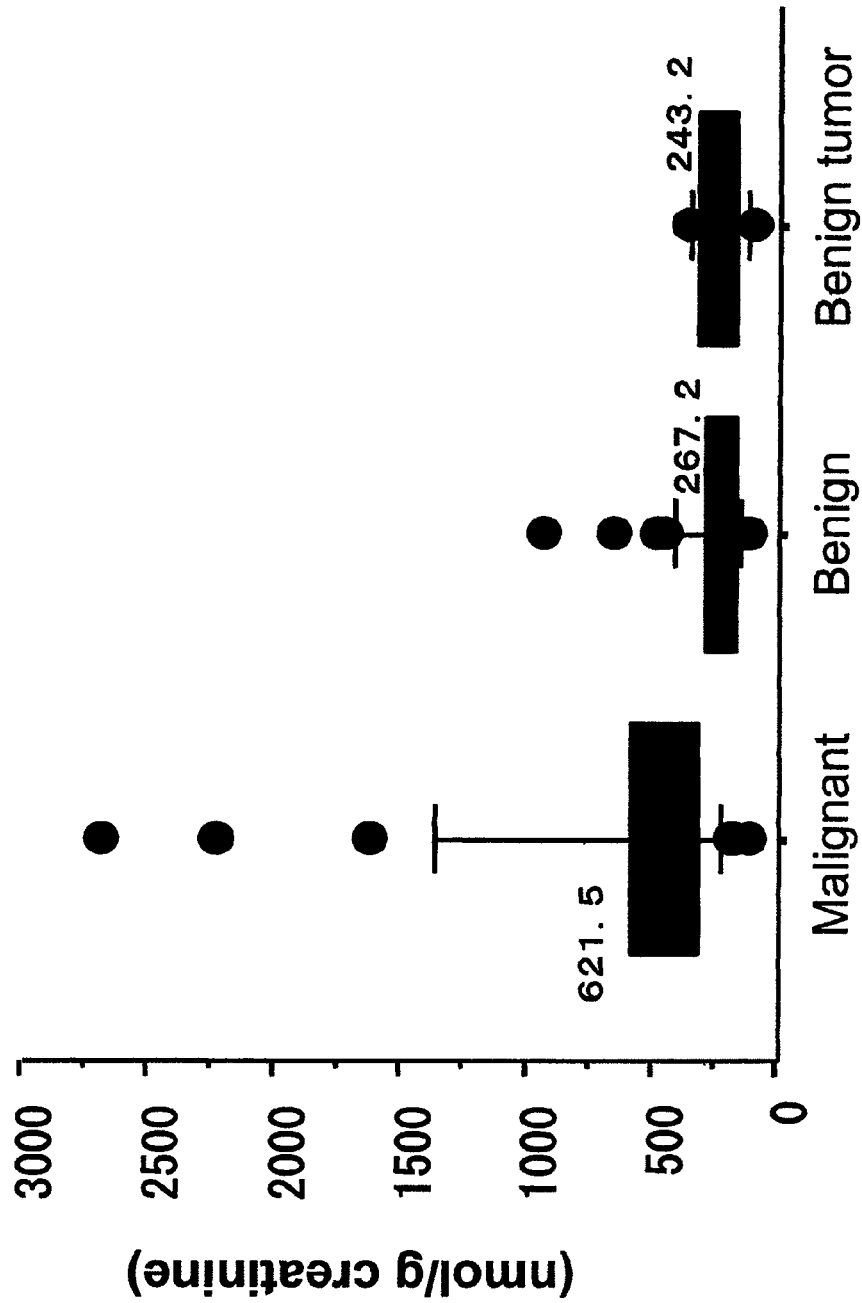
FIG. 11 is a diagram showing the relation between pancreatic/biliary tract diseases and the amount of urinary DiAcSpm.
Figure 12:
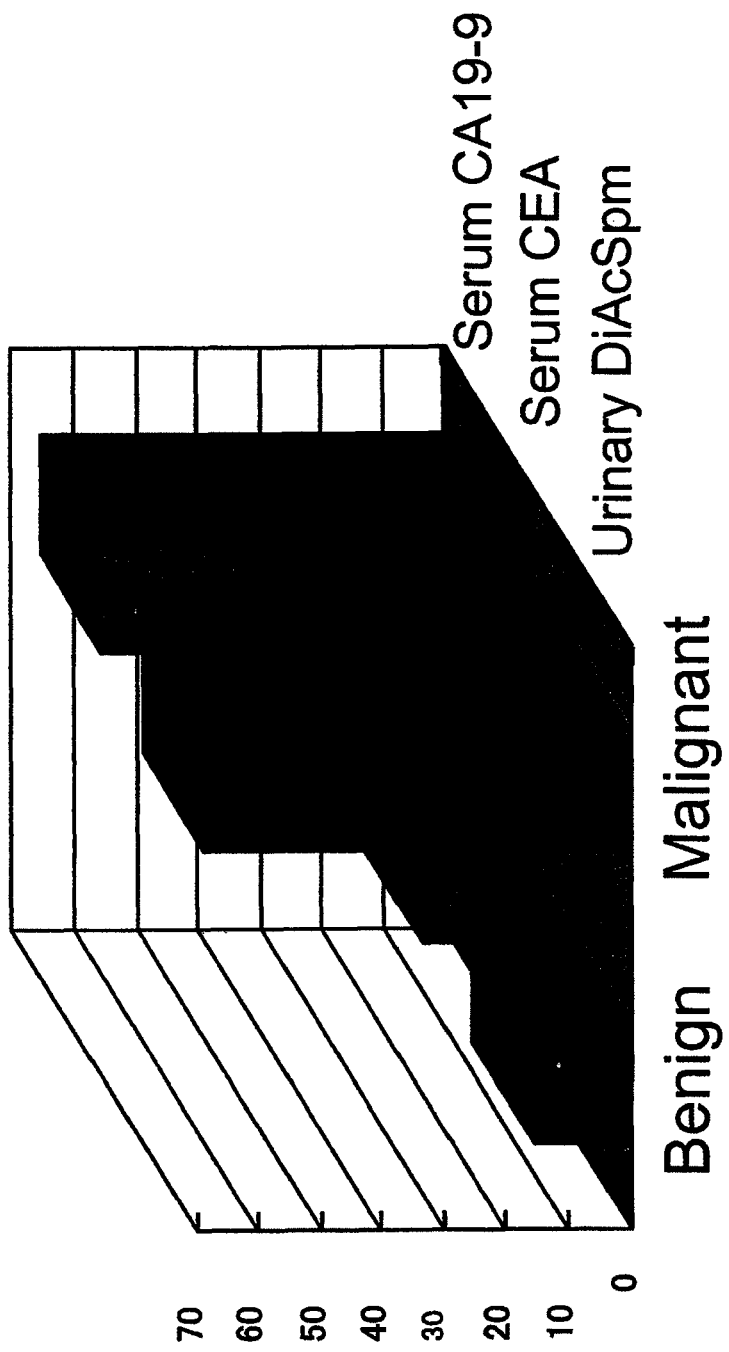
FIG. 12 is a diagram showing the positive ratios of tumor markers in benign and malignant diseases.
Figure 13:
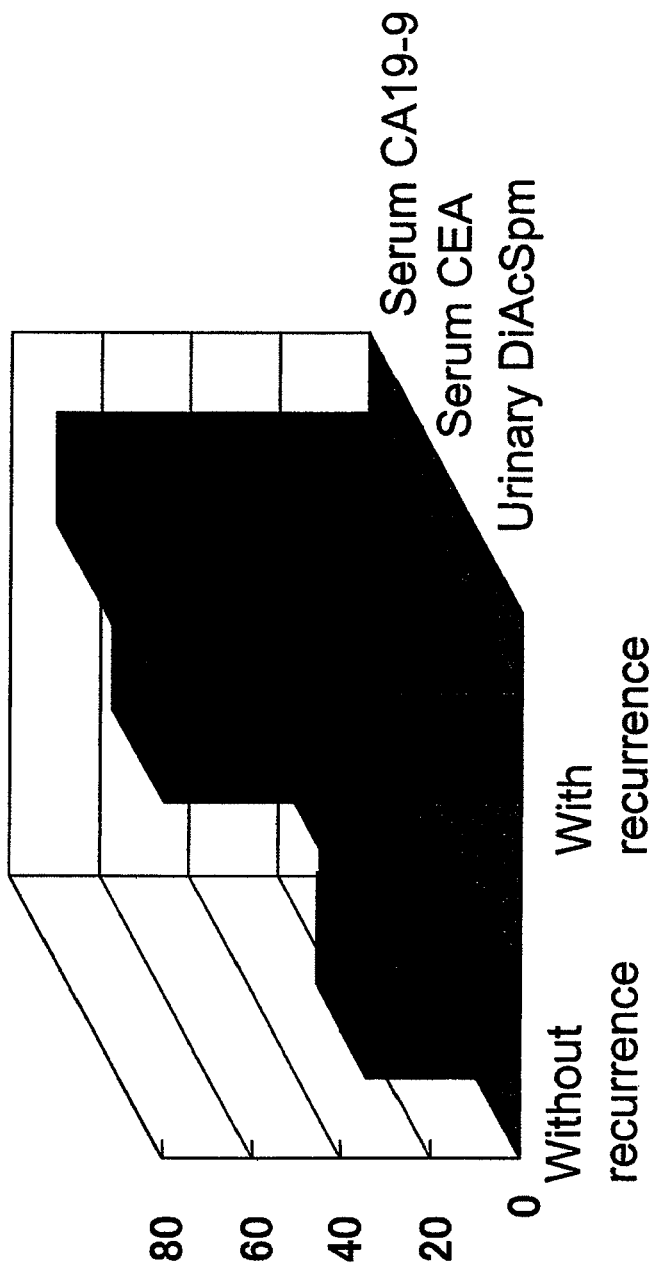
FIG. 13 is a diagram showing the positive ratios of tumor markers against recurrence of malignant tumors.
Figure 14:
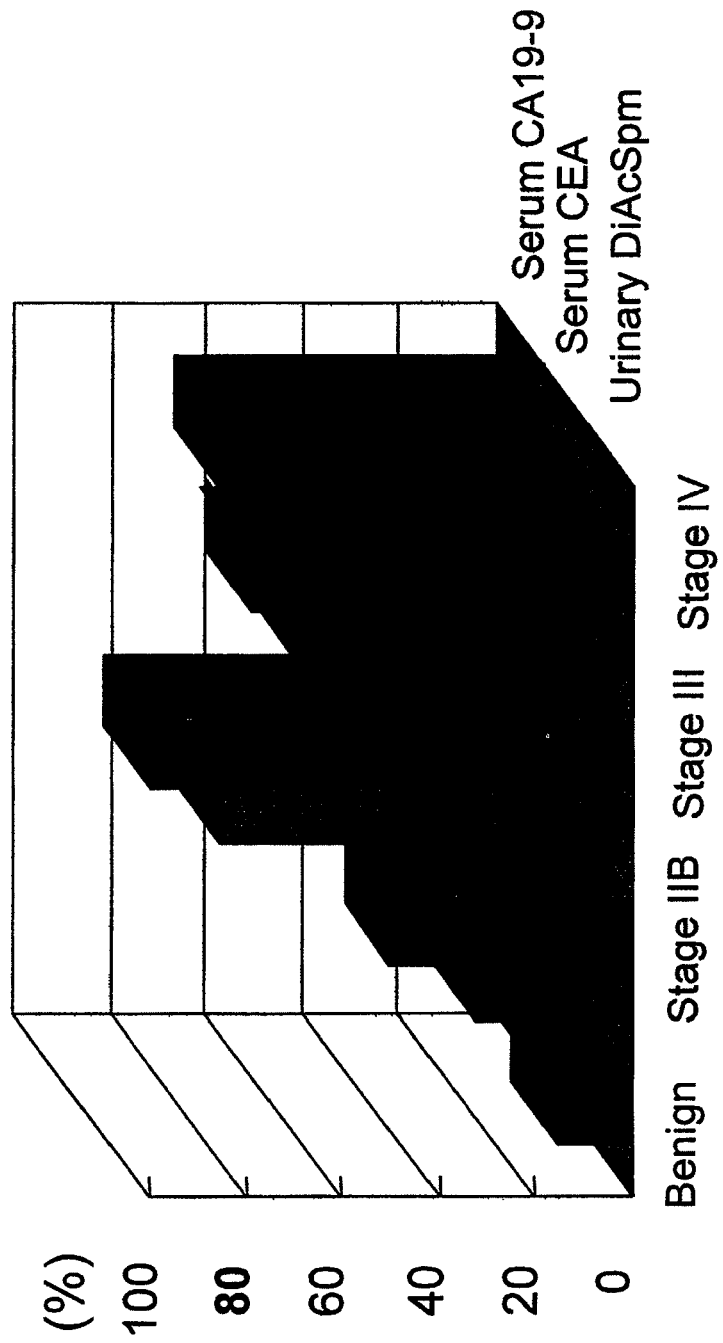
FIG. 14 is a diagram showing the relation between stages of pancreatic/biliary tract cancers and urinary or serum tumor markers.
Figure 15:
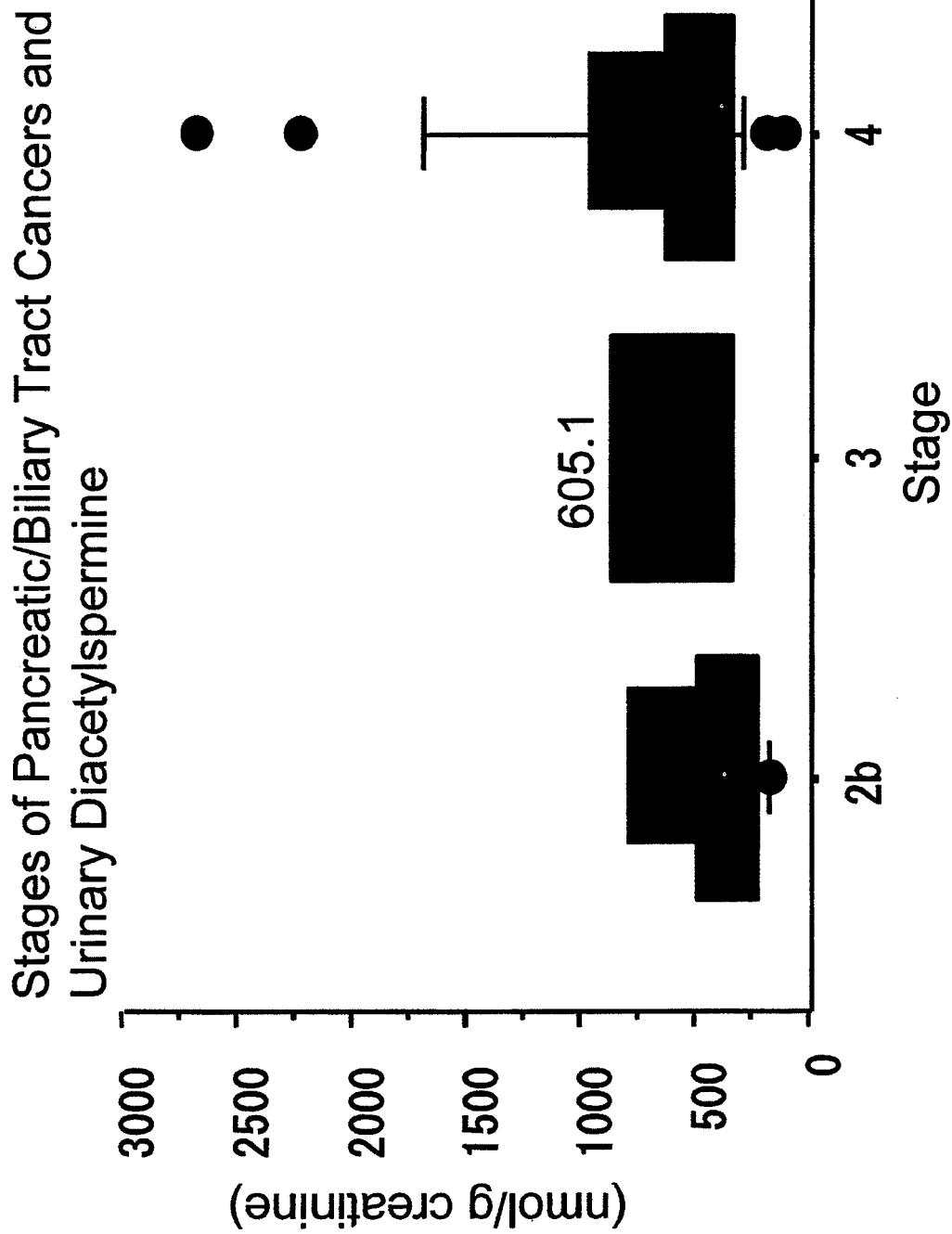
FIG. 15 is a diagram showing the relation between stages of pancreatic/biliary tract cancers and urinary DiAcSpm concentrations.

Urinary diacetylspermine levels were measured on 17 patients with breast cancer to thereby obtain the following results. When the cut-off value of diacetylspermine excreted in urine is set at 0.25 μmol/g creatinine (mean of healthy persons+2S.D.), the urinary diacetylspermine level was exceeding the cut-of value in every patient. In particular, 9 patients out of 17 showed high levels more than two times the standard value (FIG. 9). Urinary diacetylspermine has a higher positive ratio than CA15-3 that is frequently used as a tumor marker for breast cancer. This demonstrates that urinary diacetylspermine is useful as a tumor marker for detecting breast cancer with high sensitivity.

Example 5

Detection of Pancreatic/Biliary Tract Cancers

Cancer detection was carried out on 125 patients with pancreatic/biliary tract diseases. Patients with pancreatic endocrine tumor, hepatocellular carcinoma, acute inflammations (such as cholecystitis or pancreatitis) and postoperative patients who have undergone an operation within last three months were excluded from the target patients.

The particulars of the target patients are as follows.

Male: 70 cases; female: 55 cases; age: 28-86 (63.5±12.2)

Of these target patients, 52 cases were preoperative or postoperative patients with benign diseases (control); 22 cases were preoperative patients with malignant diseases; and 51 cases were postoperative patients with malignant diseases (10 patients have recurrence).

Of the above, the number of adenocarcinoma cases was 32 and the number of adenoma cases was 8.

Urinary diacetylspermine, serum CEA (high sensitivity, 2.5 ng/ml) and CA19.9 (high specificity, 37 U/ml) were detected by ELISA.

After cut-off values of urinary diacetylspermine were set, relations between the diagnosis of benign/malignant and urinary/serum tumor markers; relations between the diagnosis of recurrence and urinary/serum tumor markers; relations between stages and urinary/serum tumor markers; and relations between excision/non-excision and urinary/serum tumor markers were examined.

The results are shown in Tables 8 to 11 and FIGS. 10 to 15.

TABLE 8

Relations between Pancreatic/Biliary Tract Diseases and Urinary DiAcSpm, Serum CEA or CA19-9

| | Benign | Adenoma | Adenocarcinoma |
|---|---|---|---|
| Urinary DiAcSpm (nmol/g Creatinine) | 267.2 ± 143.0$ | 243.2 ± 96.1 | 621.5 ± 584.0$ |
| Serum | | | |
| CEA(ng/ml) | 1.2 ± 0.8 | 1.4 ± 1.2 | 39.2 ± 158.5 |
| CA19-9 | 16.8 ± 21.3# | 9.0 ± 5.07 | 825.2 ± 23,996.8# |

$p < 0.001,
P = 0.0209

TABLE 9

Relations between Benign/Malignant and Urinary DiAcSpm, Serum CEA or CA19-9

|  | DiAcSpm | | CEA | | CA19-9 | |
| --- | --- | --- | --- | --- | --- | --- |
|  | Positive | Negative | Positive | Negative | Positive | Negative |
| Malignant | 22 | 10 | 14 | 18 | 21 | 11 |
| Benign | 8 | 44 | 4 | 48 | 7 | 45 |
| Sensitivity | 75%[a] | | 44%[a] | | 75% | |
| Specificity | 81% | | 92% | | 80% | |
| Positive predictive value | 71% | | 78% | | 86% | |
| Negative predictive value | 84% | | 73% | | 87% | |
| Efficacy | 79% | | 74% | | 79% | |

[a]$P = 0.044$

TABLE 10

Relations between Recurrence and Urinary DiAcSpm, Serum CEA or CA19-9

|  | DiAcSpm | | CEA | | CA19-9 | |
| --- | --- | --- | --- | --- | --- | --- |
| Recurrence | Positive | Negative | Positive | Negative | Positive | Negative |
| Present | 8 | 2 | 7 | 3 | 7 | 3 |
| None | 14 | 27 | 9 | 32 | 7 | 34 |
| Sensitivity | 80% | | 70% | | 70% | |
| Specificity | 66% | | 78% | | 83% | |
| Positive predictive value | 36% | | 44% | | 50% | |
| Negative predictive value | 93% | | 91% | | 92% | |
| Efficacy | 69% | | 76% | | 80% | |

TABLE 11

Relations between Tumor Stages and Urinary DiAcSpm, Serum CEA or CA19-9

| Stage | DiAcSpm | | CEA | | CA19-9 | |
| --- | --- | --- | --- | --- | --- | --- |
|  | Positive | Negative | Positive | Negative | Positive | Negative |
| IIb | 3 | 3 | 0 | 6 | 4 | 2 |
| III | 2 | 0 | 1 | 1 | 1 | 1 |
| IV | 19 | 5 | 11 | 13 | 16 | 8 |

As shown in above Tables 8 to 11 and FIGS. 10 to 15, urinary diacetylspermine shows high sensitivity against pancreatic/biliary tract cancers almost equivalent to that of serum CA19-9 which is regarded as a highly sensitive tumor marker. Urinary diacetylspermine, which does not required collection of blood samples, can be said a "universal" tumor marker without organ specificity. Besides, urinary diacetylspermine is a tumor marker useful in mass-screening and examination of high risk groups.

Even at Stage IIB (a relatively early stage), urinary diacetylspermine indicated positive in 50%, which demonstrates that urinary diacetylspermine was also effective in detecting early pancreatic/biliary tract cancers.

Example 6

Measurement of Diacetylspermine by Stage of Breast Cancer

In this Example, relations between stages of breast cancer and urinary DiAcSpm levels (creatinine-corrected values of concentrations in random urine) were examined on 83 patients with breast cancer. Stages of breast cancer and contents thereof are as described in Table 12.

TABLE 12

Stages of Breast Cancer (based on TNM classification)

| Stage | Contents |
| --- | --- |
| 0 | Non-invasive cancer or Paget's disease with no tumor. |
| I | Tumor 2 cm or less in size, and no evidence of metastasis to lymph nodes under the arm. |
| IIA | Tumor 2 cm or less in size, and evidence of metastasis to lymph nodes under the arm. Tumor more than 2 cm but not more than 5 cm, and no evidence of metastasis to lymph nodes under the arm. |
| IIB | Tumor more than 2 cm but not more than 5 cm, and evidence of metastasis to lymph nodes under the arm. Tumor more than 5 cm, and no evidence of metastasis to lymph nodes under the arm. |
| IIIA | Tumor more than 5 cm, and evidence of metastasis to lymph nodes under the arm. Regardless of the size of tumor, metastases to the under arm lymph nodes fixed to one another or to other structures are observed. |

TABLE 12-continued

Stages of Breast Cancer (based on TNM classification)

| Stage | Contents |
|---|---|
| IIIB | Tumor fixed on the chest wall with no movement; edema or ulceration of the skin or satellite skin nodules are observed.<br>Evidence of metastases to parasternal lymph nodes (lymph nodes around the artery behind the sternum).<br>Breast cancer accompanied with redness, edema, pain, etc. like in mastitis (inflammatory breast cancer); easily mistaken as inflammation. |
| IV | Evidence of metastases to supraclavicular lymph nodes.<br>Accompanies with metastases to other distant organs (distant organs such as bone, lung or liver, and distant lymph nodes other than supraclavicular lymph nodes)<br>Stages 0 to IIIB have no distant metastasis. |

Of the above-mentioned breast cancer patients, 15 patients were at stage I; 15 patients were at stage I; 4 patients were at stage III; and 47 patients were at stage IV. The cut-off value of DiAcSpm was set at 0.25 μmol/g creatinine (mean of healthy persons+2SD). DiAcSpm levels exceeding this were regarded as positive, and DiAcSpm levels below this were regarded as negative.

The results are shown in Table 13.

TABLE 13

Positive Ratio of Urinary DiAcSpm by Stage of Breast Cancer

|  | Positive | Negative | Positive ratio (%) |
|---|---|---|---|
| stage I | 3 | 12 | 20 |
| stage II | 6 | 11 | 35 |
| stage III | 3 | 1 | 75 |
| stage IV | 38 | 9 | 81 |
| Total | 50 | 33 |  |

Relations between the stage of breast cancer and serum CEA levels were examined on the same group of patients as examined above. The standard value of CEA was set at 5 ng/ml, and levels exceeding this were regarded as positive, and levels below this were regarded as negative.

The results are shown in Table 14.

TABLE 14

Positive Ratio of Serum CEA by Stage of Breast Cancer

|  | Positive | Negative | Positive Ratio (%) |
|---|---|---|---|
| stage I | 0 | 15 | 0 |
| stage II | 1 | 16 | 6 |
| stage III | 2 | 2 | 50 |
| stage IV | 28 | 19 | 60 |
| Total | 31 | 52 |  |

Relations between the stage of breast cancer and serum CA15-3 levels were examined on the same group of patients as examined above. The standard value of CA15-3 was set at 23 U/ml, and levels exceeding this were regarded as positive, and levels below this were regarded as negative.

The results are shown in Table 15.

TABLE 15

Positive Ratio of Serum CA15-3 by Stage of Breast Cancer

|  | Positive | Negative | Positive Ratio (%) |
|---|---|---|---|
| stage I | 0 | 15 | 0 |
| stage II | 0 | 17 | 0 |
| stage III | 2 | 2 | 50 |
| stage IV | 29 | 18 | 62 |
| Total | 31 | 52 |  |

As shown in above Tables 13 to 15, at any stage of early cancer and advanced cancer, the urinary DiAcSpm level in the urine of breast cancer patients showed a high positive ratio. In particular, the positive ratios of 20-35% at stage I and stage II are comparable to the positive ratios obtained by examination with PET (positron emission tomography). The obtained DiAcSpm levels, CEA levels and CA15-3 levels were compared at the relatively early stage (a group combining stages I and II) and the advanced cancer stage (a group combining stages III and IV).

The results are shown in Table 16.

TABLE 16

Positive Ratios of DiAcSpm and Tumor Markers at Early and Advanced Stages of Breast Cancer

| Stage | n | DiAcSpm | | | CEA | | | CA15-3 | | |
|---|---|---|---|---|---|---|---|---|---|---|
|  |  | Positive | Negative | Positive ratio (%) | Positive | Negative | Positive ratio (%) | Positive | Negative | Positive ratio (%) |
| I + II | 32 | 9 | 23 | 28.1 | 1 | 31 | 3.1 | 0 | 32 | 0 |
| III + IV | 51 | 41 | 10 | 80.3 | 30 | 21 | 58.8 | 31 | 20 | 60.8 |
| Total | 83 | 50 | 33 | 60.2 | 31 | 52 | 37.3 | 31 | 52 | 37.3 |

As shown in Table 16, the respective positive ratios at the relatively early stage were 28.1% in DiAcSpm level, 3.1% in CEA level, and 0% in CA15-3 level. Significant difference was observed both between DiAcSpm level and CEA level ($p=0.0064$) and between DiAcSpm level and CA15-3 level ($p=0.0010$). Similarly, the respective positive ratios at the advanced stage were 80.3% in DiAcSpm level, 58.8% in CEA level, and 60.8% in CA15-3 level. Significant difference was observed both between DiAcSpm level and CEA level ($p=0.018$) and between DiAcSpm level and CA15-3 level ($p=0.030$). As a whole, the respective positive ratios were 60.2% in DiAcSpm level and 37.3% in both CEA level and CA15-3 level. Significant difference was observed between DiAcSpm level and either CEA or CA15-3 level with $p=0.0032$. Therefore, it was demonstrated that DiAcSpm detects breast cancer with by far higher sensitivity, even compared with existing tumor markers CEA and CA15-3 now used clinically.

Example 7

Detection of Various Cancers

In this Example, cancers in the pancreas/biliary tract, lung, liver, uterus and blood were detected. The cut-off value was set at 325 (nmol/g creatinine). With respect to pancreatic cancer and biliary tract cancer, test samples different from those in Example 5 were used.

The results are shown in Table 17.

TABLE 17

| Cancer species | Number of positive samples | Positive ratio (%) |
| --- | --- | --- |
| Pancreatic cancer, Biliary tract cancer | 39/53 | 74 |
| Lung cancer | 29/35 | 83 |
| Liver cancer | 31/49 | 63 |
| Uterine cervix cancer | 10/15 | 67 |
| Myelogenous leukemia | 4/6 | 67 |

As shown in Table 17, with the use of the kit of the invention, it was possible to detect not only colorectal cancer and breast cancer but also lung cancer, liver cancer, uterine cervix cancer and myelogenous leukemia (chronic and acute) with high positive ratios.

Example 8

Detection of Various Brain Tumors

In this Example, positive ratios of urinary DiAcSpm in various brain tumors were measured. The results are shown in Table 18.

TABLE 18

| Cancer species | Number of positive samples | Positive ratio (%) |
| --- | --- | --- |
| Metastatic brain tumor | 30/33 | 90.9 |
| Grade 2 glioma | 1/2 | 50 |
| Grade 3 glioma | 6/8 | 75 |
| Grade 4 glioma | 4/4 | 100 |
| Glioma overall | 11/14 | 78.6 |
| Primary malignant lymphoma of central nerve system | 3/3 | 100 |

The positive ratio of metastatic brain tumor was fairly high. In glioma, the positive ratio rose as the grade rises from 2 to 4 one by one (i.e., malignancy increases). Further, the DiAcSpm levels per se became fairly high at that time.

Example 9

Detection of Primary Malignant Lymphoma of Brain

In this Example, DiAcSpm was detected from samples collected from patients with primary malignant lymphoma of the brain.

(1) Case 1 (Female, Age 56, Primary Malignant Lymphoma of the Brain)

Figure 16:
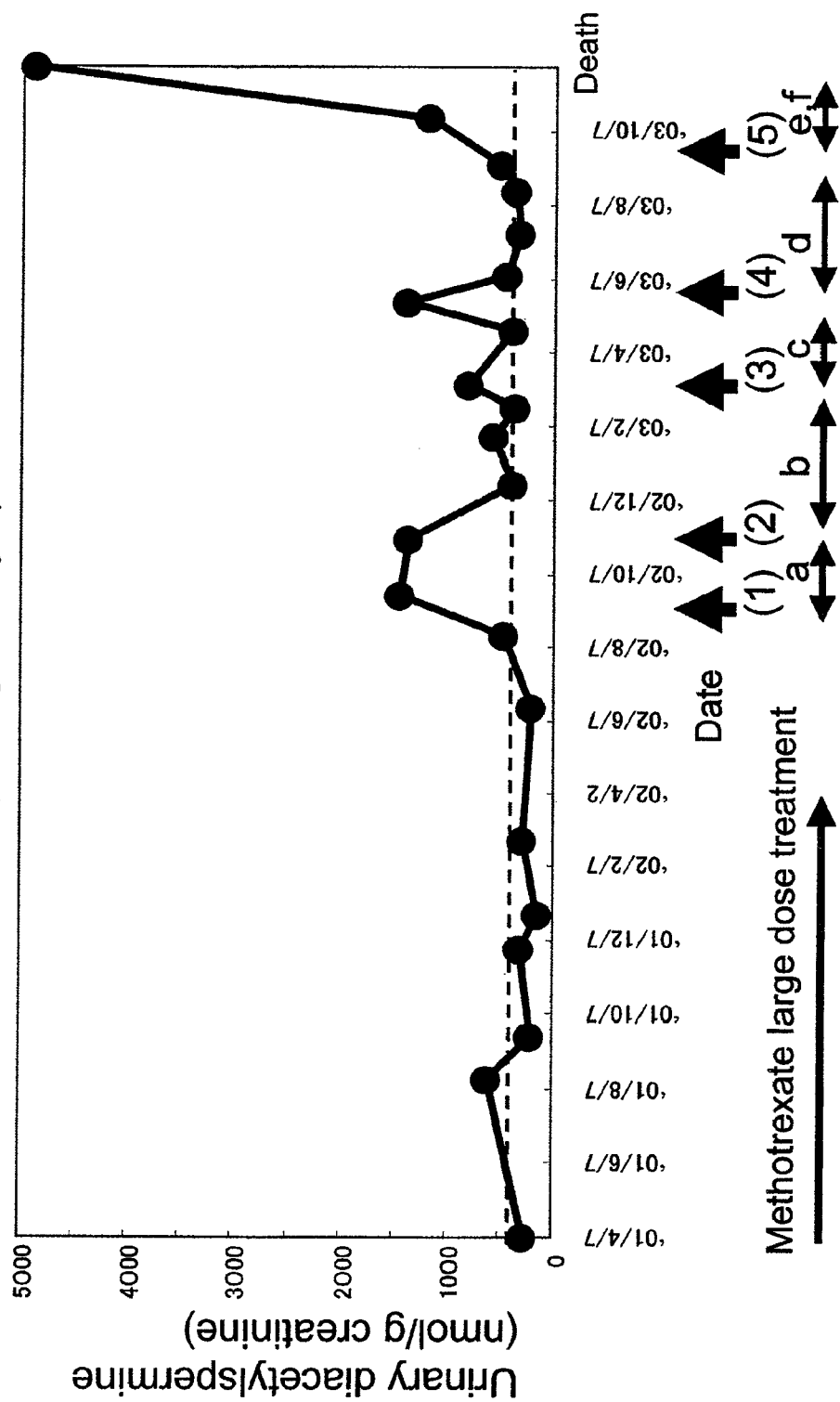
FIG. 16 is a diagram showing the time course of urinary DiAcSpm levels which reflect the conditions and treatment effects of a patient with primary malignant lymphoma of the brain.
Figure 17:
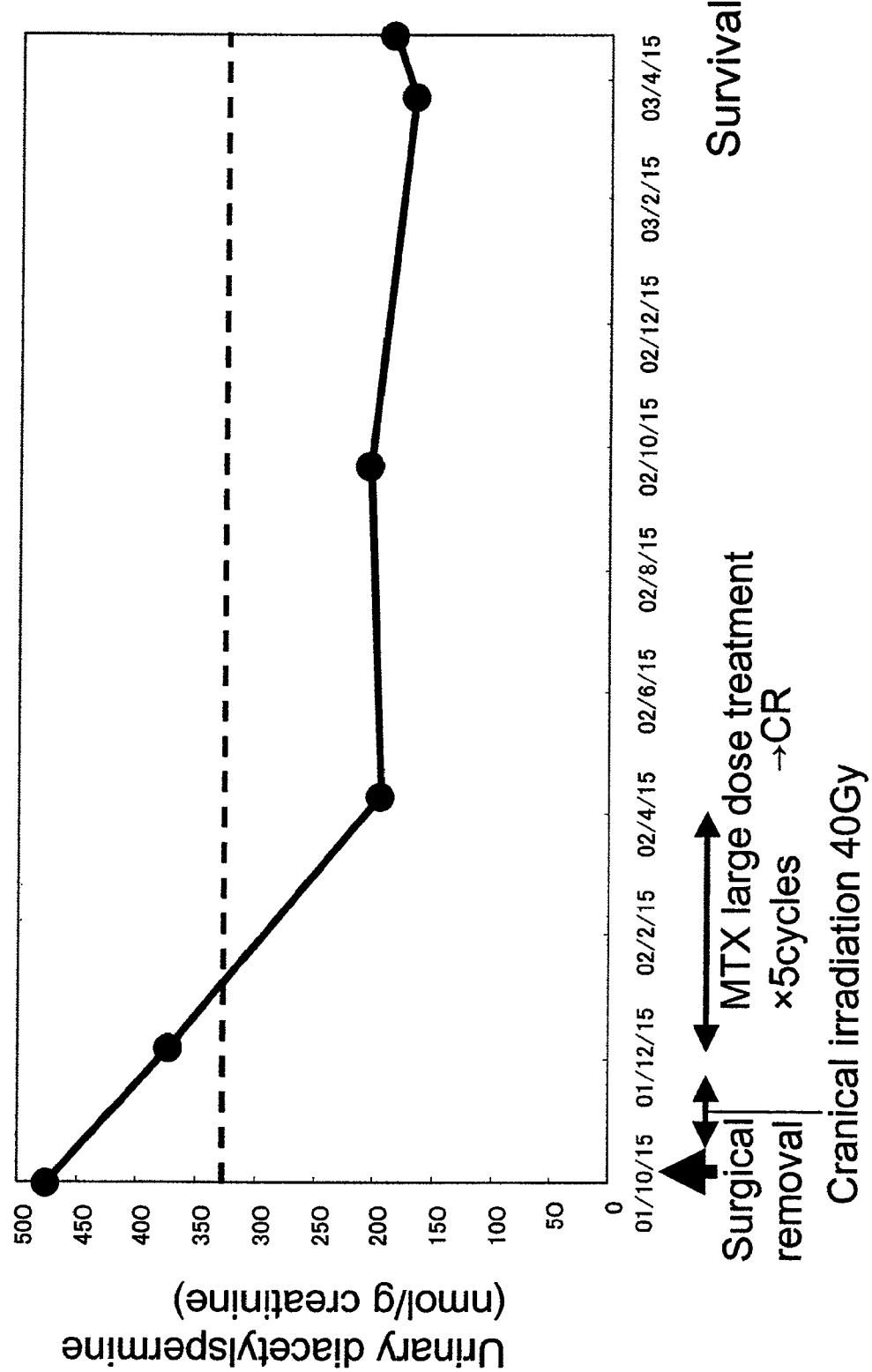
FIG. 17 is a diagram showing the time course of urinary DiAcSpm levels which reflect the conditions and treatment effects of a patient with primary malignant lymphoma of the brain.

This patient has undergone cranial irradiation and methotrexate (MTX) large dose treatment against primary malignant lymphoma of the brain as early treatment. At the start of DiAcSpm measurement, incipient lesions were in the state of complete remission (CR). However, metastases to the bone marrow and the spleen became evident on images and as conditions at time points (1) and (2) indicated in FIG. 16. At those points, a sharp elevation of DiAcSpm was recognized. This degree of elevation was higher than that of β-2 microglobulin, a commonly used marker. Since time point (2), reactions to the treatment (Table 19) began to be seen and the DiAcSpm level was lowered. At time points (3) and (4), treatment against recurrence became difficult. Besides, periods of partial remission (PR) became gradually shorter, and the DiAcSpm levels were not completely lowered. At time point (5), tumor was completely showing resistance to treatment, and the DiAcSpm level rose sharply.

Relations between recurrence, treatments and reactions (exitus) are shown in Table 19. In Table 19, items (1) to (5) and a) to f) correspond to those shown in FIG. 16.

TABLE 19

| Recurrence site | Treatment | Reaction |
| --- | --- | --- |
| (1) Spinal dissemination | a) Anterior spinal irradiation at 36 Gy | CR |
| (2) Metastasis to the spleen | b) ESHAP chemotherapy × 3 | CR |
| (3) Intracerebral recurrence (left frontal lobe) | c) Fractionated partial irradiation at 20 Gy | PR |
| (4) Dissemination in the medullary cavity | d) Administration of MTX & Ara-C into the medullary cavity | PR |
| (5) Intracerebral recurrence (callosum) | e) Fractionated partial irradiation at 20 Gy<br>f) Ara-C large dose treatment | PD |

(2) Case 2 (Male, Age 60, Primary Malignant Lymphoma of the Brain)

DiAcSpm levels were high until the start of treatment. Then, tumor tissues in the right frontal lobe were removed surgically, followed by cranial irradiation at 40 Gy and 5 cycles of MTX large dose treatment. As a result, complete remission was achieved. At this point, DiAcSpm level decreased below the cut-off value.

Therefore, it was shown that DiAcSpm can be a definite marker for the treatment effect of early treatment of brain tumor.

(3) Conclusion

In the diagnosis of malignant lymphoma, problems such as described below are enumerated.

(i) Even if the tumor can be judged CR on images, there is a high possibility that tumor cells capable of proliferation are still remaining in the central nerve;

(ii) Even if the remnant of lesions may be grasped on images, tumor cells may no longer exist; and (iii) The tumor may metastasize to organs other than the brain.

The present invention can solve above problems. By measuring the positive ratio of DiAcSpm, it is possible to detect the presence or absence of tumor cells regardless of lesions grasped on images. Therefore, it becomes possible to judge when and to what extent chemotherapy should be carried out against malignant lymphoma. Besides, by using DiAcSpm as an indicator, it is possible to grasp those cases where conversion to malignancy occurs during the process of treatment of cancer. Therefore, it is possible to diagnose the recurrence of cancer or predict prognosis, which enables establishment of appropriate treatment policy. Further, the kit of the present invention is not only capable of screening cancer or making preoperative diagnosis but also capable of detecting therapeutic effect, recurrence, conversion to malignancy, etc. even in those cases where histological diagnosis has been established.

Example 10

Detection of Astrocytoma

In this Example, DiAcSpm was measured in a patient (age 36, male) with grade 3 astrocytoma (a kind of glioma) after he received a surgical operation for recurred tumor (FIG. 18).

After the operation, tumor was remaining but urinary DiAcSpm did not show high levels.

No big changes were observed after irradiation treatment and chemotherapy. Even when radiation necrosis occurred, no elevation of DiAcSpm was recognized. On the other hand, when the callosal expanded because of recurrence and clinical malignancy of tumor was clearly accelerated, DiAcSpm level began to rise sharply. In glioma, conversion from grade 3 to grade 4 frequently occurs. It is often difficult to prove this conversion by diagnostic imaging or with pathological tissues (e.g., to discriminate between radiation necrosis and recurred lesions by diagnostic imaging). In the present invention, it was possible to discriminate between the above-mentioned radiation necrosis and the presence/absence of recurred lesions by detecting urinary DiAcSpm. Therefore, it was demonstrated that detection of DiAcSpm is extremely useful clinically as an indicator of the degree of malignancy.

INDUSTRIAL APPLICABILITY

According to the present invention, DiAcSpm as a tumor marker is provided. Further, according to the present invention, an antibody in which total interference on the measurement results caused by its cross-reaction with DiAcSpm analogues is extremely small and which specifically binds to a trace amount of DiAcSpm; and a kit comprising the antibody are also provided. The kit of the present invention is extremely useful because this kit is capable of detecting the presence or absence of various cancers, the degree of malignancy of cancers, the presence or absence of recurrence, etc. by using the positive ratio of DiAcSpm as an indicator.

The invention claimed is:

1. A method of detecting colorectal cancer of stages 0 to I, an early tumor, comprising
    taking a biological sample from a patient suspected of having the colorectal cancer or subject of a health examination;
    contacting the biological sample with an antibody that binds $N^1,N^{12}$-diacetylspermine, thereby binding the antibody with $N^1,N^{12}$-diacetylspermine in the biological sample;
    quantitatively determining $N^1,N^{12}$-diacetylspermine contained in the biological sample on the basis of quantitative determination results of the antibody which is bound to $N^1,N^{12}$-diacetylspermine; and
    detecting the presence or absence of the colorectal cancer of stages 0 to I using the quantitative determination results of $N^1,N^{12}$-diacetylspermine as an indicator.

2. The method according to claim 1, wherein the biological sample is urine.

3. The method according to claim 1, wherein the cancer detected is colorectal cancer of stages 0 to I.

4. A method of detecting colorectal cancer of stages 0 to I, an early tumor, comprising
    providing a $N^1,N^{12}$-diacetylspermine specific antibody which has at least one property selected from the group consisting of (a) a cross-reactivity with $N^1$-acetylspermidine of 0.1% or less, and (b) a total interference on the measurement of $N^1,N^{12}$-diacetylspermine specific antibody caused by its cross-reaction with $N^1$-acetylspermidine, $N^8$-acetylspermidine, $N^1,N^8$-diacetylspermidine, and acetylspermine present in urine of 5% or less;
    contacting a biological sample from a patient suspected of having the colorectal cancer or subject of a health examination with the antibody, thereby binding the antibody with $N^1,N^{12}$-diacetylspermine in the biological sample;
    quantitatively determining $N^1,N^{12}$-diacetylspermine contained in the biological sample on the basis of quantitative determination results of the antibody bound to $N^1,N^{12}$-diacetylspermine; and
    detecting the presence or absence of the colorectal cancer of stages 0 to I using the quantitative determination results of $N^1,N^{12}$-diacetylspermine as an indicator.

5. The method according to claim 4, wherein the biological sample is urine.

6. The method according to claim 4, wherein the cancer detected is colorectal cancer of stages 0 to I.

7. The method according to claim 4, wherein the total interference (b) is 3% or less.

* * * * *